United States Patent
Imamura

(10) Patent No.: US 9,320,424 B2
(45) Date of Patent: Apr. 26, 2016

(54) IMAGE DISPLAY APPARATUS, IMAGE DISPLAY METHOD AND IMAGING SYSTEM

(71) Applicant: CANON KABUSHIKI KAISHA, Tokyo (JP)

(72) Inventor: Hiroshi Imamura, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 14/370,519

(22) PCT Filed: Feb. 13, 2013

(86) PCT No.: PCT/JP2013/054062
§ 371 (c)(1),
(2) Date: Jul. 3, 2014

(87) PCT Pub. No.: WO2013/125546
PCT Pub. Date: Aug. 29, 2013

(65) Prior Publication Data
US 2014/0340638 A1    Nov. 20, 2014

(30) Foreign Application Priority Data
Feb. 20, 2012   (JP) .................................. 2012-034536

(51) Int. Cl.
*A61B 3/00* (2006.01)
*A61B 5/024* (2006.01)
(Continued)

(52) U.S. Cl.
CPC ............. *A61B 3/0058* (2013.01); *A61B 3/0025* (2013.01); *A61B 3/1025* (2013.01);
(Continued)

(58) Field of Classification Search
CPC .. A61B 3/1233; A61B 3/1241; A61B 3/1225; A61B 3/14; A61B 3/145; A61B 3/0025; A61B 3/1015; A61B 3/00; A61B 3/12; A61B 3/0058; A61B 3/1025; A61B 5/00; A61B 5/0059; A61B 5/0062; A61B 5/0066; A61B 5/0068; A61B 5/02007; A61B 5/02014; A61B 5/026; A61B 5/02416; A61B 5/0261; G06K 9/00127; G06T 3/4038; G06T 7/0012; G06T 7/0014; G06T 7/0016; G06T 7/0024; G06T 7/2006; G06T 7/2053; G06T 2200/24; G06T 2207/20016; G06T 2207/20148; G06T 2207/30041; G06T 2207/30101; G06T 2207/30104
USPC .................. 351/206–208, 221, 246; 382/134; 396/18; 600/504
See application file for complete search history.

(56) References Cited

U.S. PATENT DOCUMENTS 7,488,294 B2   2/2009   Torch
7,515,054 B2   4/2009   Torch
(Continued)

FOREIGN PATENT DOCUMENTS

CN   1045028 A   9/1990
CN   1960670 A   5/2007
(Continued)

OTHER PUBLICATIONS

Apr. 2, 2013 International Search Report and Written Opinion in International Patent Appln. No. PCT/JP2013/054062.
(Continued)

*Primary Examiner* — Ricky Mack
*Assistant Examiner* — Gary O'Neill
(74) *Attorney, Agent, or Firm* — Fitzpatrick, Cella, Harper & Scinto

(57) ABSTRACT

An image display apparatus obtains a plurality of moving images obtained by capturing a plurality of imaging areas of a fundus, and a wide field of view image obtained by capturing an area including the plurality of imaging areas of the fundus. Each of the plurality of moving images is associated with pulse data based on a biomedical signal obtained in capturing the moving image. The image display apparatus superimposes and displays at least one frame of each of the plurality of moving images at a position on the wide field of view image, which is determined based on information about the positions of the plurality of imaging areas. In the superimposing/display operation, the image display apparatus displays the plurality of moving images at a display timing synchronized based on the pulse data.

20 Claims, 14 Drawing Sheets

(51) Int. Cl.
  *A61B 5/026*  (2006.01)
  *G06T 7/00*  (2006.01)
  *G06T 3/40*  (2006.01)
  *A61B 3/14*  (2006.01)
  *A61B 3/10*  (2006.01)
  *A61B 3/12*  (2006.01)

(52) U.S. Cl.
  CPC ............... *A61B3/1241* (2013.01); *A61B 3/145* (2013.01); *A61B 5/0261* (2013.01); *A61B 5/02416* (2013.01); *G06T 3/4038* (2013.01); *G06T 7/0014* (2013.01); *G06T 7/0024* (2013.01); *A61B 3/1015* (2013.01); *A61B 3/1233* (2013.01); *G06T 2200/24* (2013.01); *G06T 2207/20016* (2013.01); *G06T 2207/30041* (2013.01)

(56) References Cited

U.S. PATENT DOCUMENTS

| | | | |
|---|---|---|---|
| 8,235,528 | B2 | 8/2012 | Mukai et al. |
| 8,840,248 | B2 | 9/2014 | Imamura |
| 2006/0122524 | A1 | 6/2006 | Kawada et al. |
| 2007/0273611 | A1 | 11/2007 | Torch |
| 2009/0018419 | A1 | 1/2009 | Torch |
| 2009/0058660 | A1 | 3/2009 | Torch |
| 2010/0277692 | A1 | 11/2010 | Mukai et al. |
| 2011/0134393 | A1 | 6/2011 | Iwase |
| 2011/0137157 | A1 | 6/2011 | Imamura et al. |
| 2011/0234978 | A1* | 9/2011 | Hammer et al. .............. 351/208 |
| 2012/0063660 | A1 | 3/2012 | Imamura et al. |
| 2012/0130270 | A1 | 5/2012 | Imamura et al. |
| 2013/0058553 | A1 | 3/2013 | Yonezawa et al. |
| 2013/0070201 | A1* | 3/2013 | Shahidi et al. ................ 351/206 |
| 2014/0085606 | A1 | 3/2014 | Miyasa et al. |
| 2014/0240667 | A1 | 8/2014 | Uji et al. |
| 2014/0240668 | A1 | 8/2014 | Uji et al. |
| 2014/0240669 | A1 | 8/2014 | Imamura |

FOREIGN PATENT DOCUMENTS

| | | |
|---|---|---|
| CN | 101181152 A | 5/2008 |
| CN | 101926640 A | 12/2010 |
| JP | 05-192299 A | 8/1993 |
| JP | 2010-259543 A | 11/2010 |
| JP | 2011-005312 A | 1/2011 |
| JP | 2011-120657 A | 6/2011 |
| WO | 2004/004556 A1 | 1/2004 |
| WO | 2009/148067 A1 | 12/2009 |
| WO | 2011/066546 A1 | 6/2011 |

OTHER PUBLICATIONS

Akihito Uji, et al., Japanese Society of Ophthalmological Optics, Abstracts, vol. 47 (2011), p. 55.

Nov. 3, 2015 Chinese Official Action in Chinese Patent Appln.No. 201380010115.2.

* cited by examiner

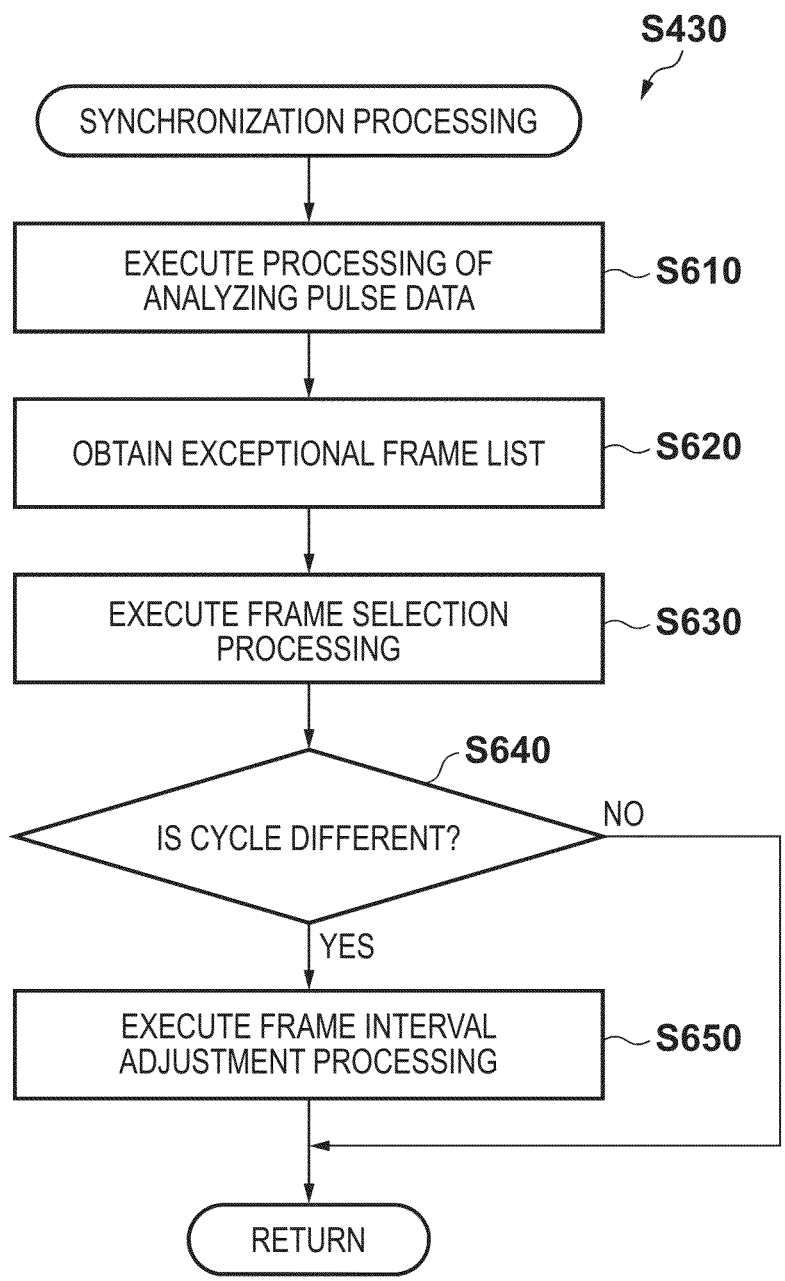

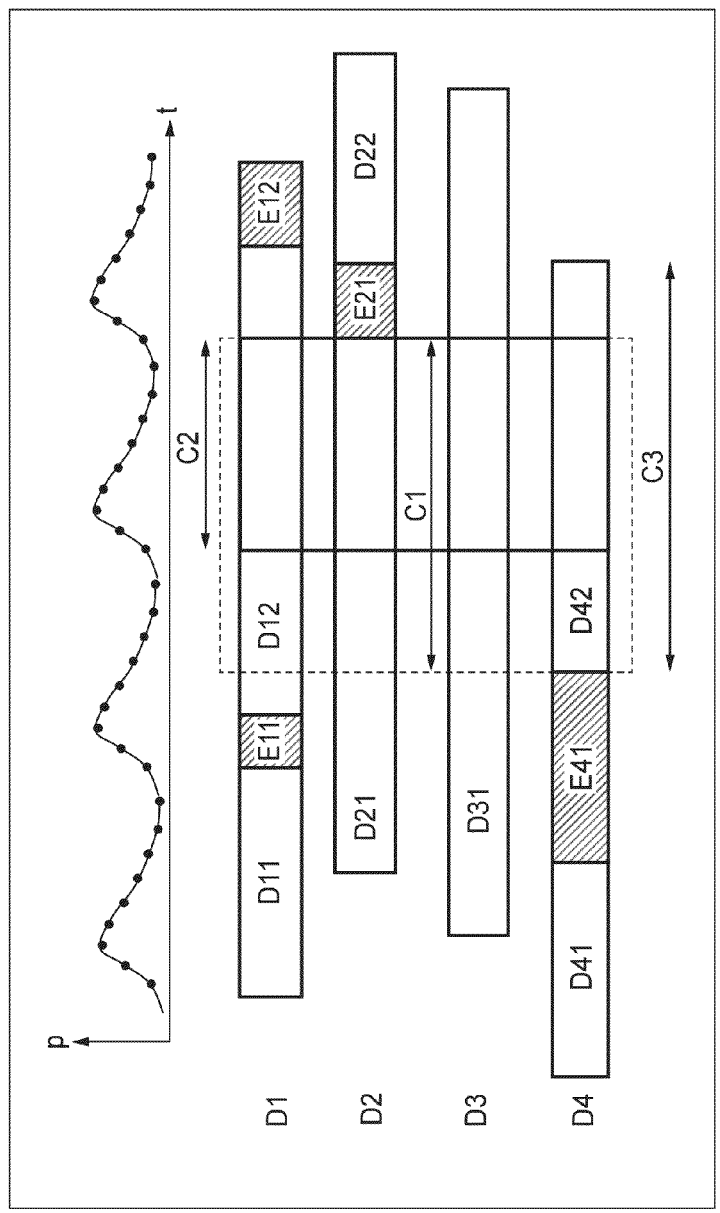 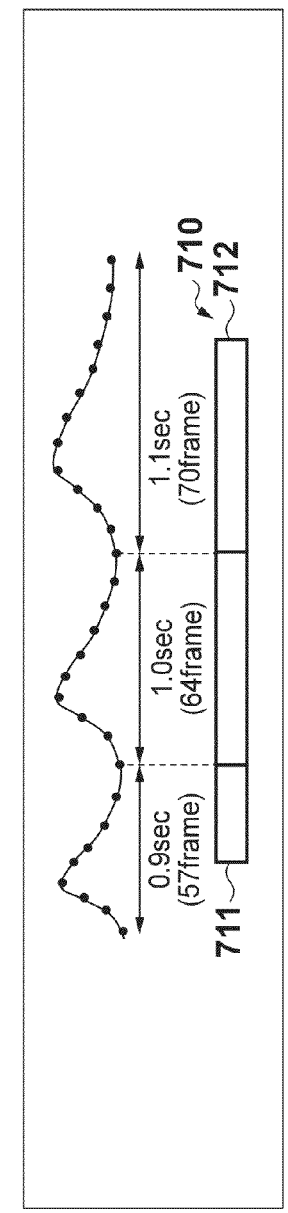
FIG. 7A
FIG. 7B

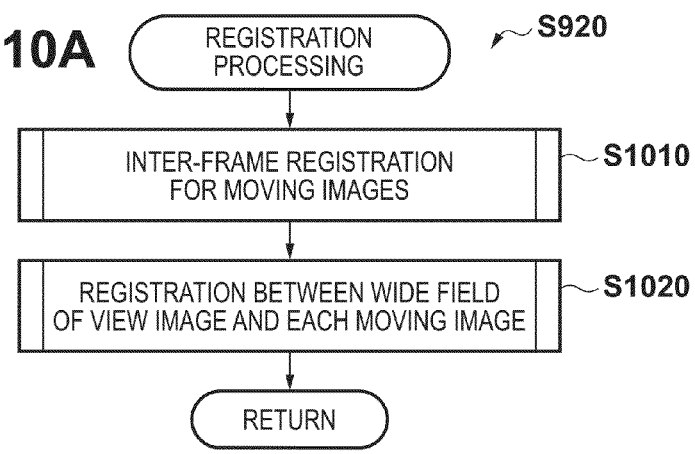
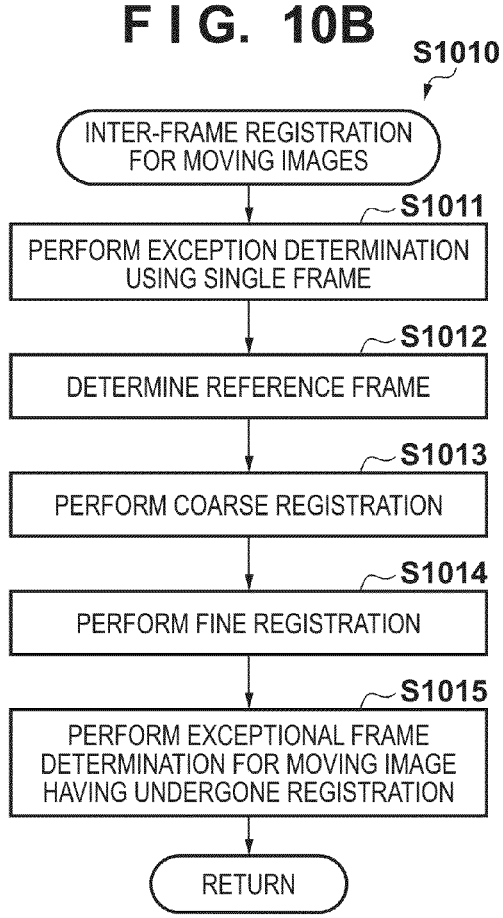
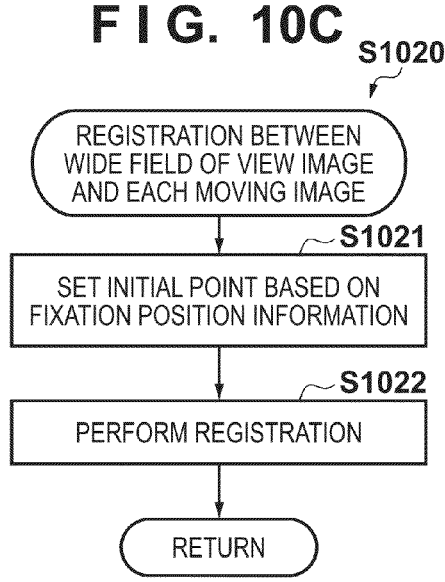

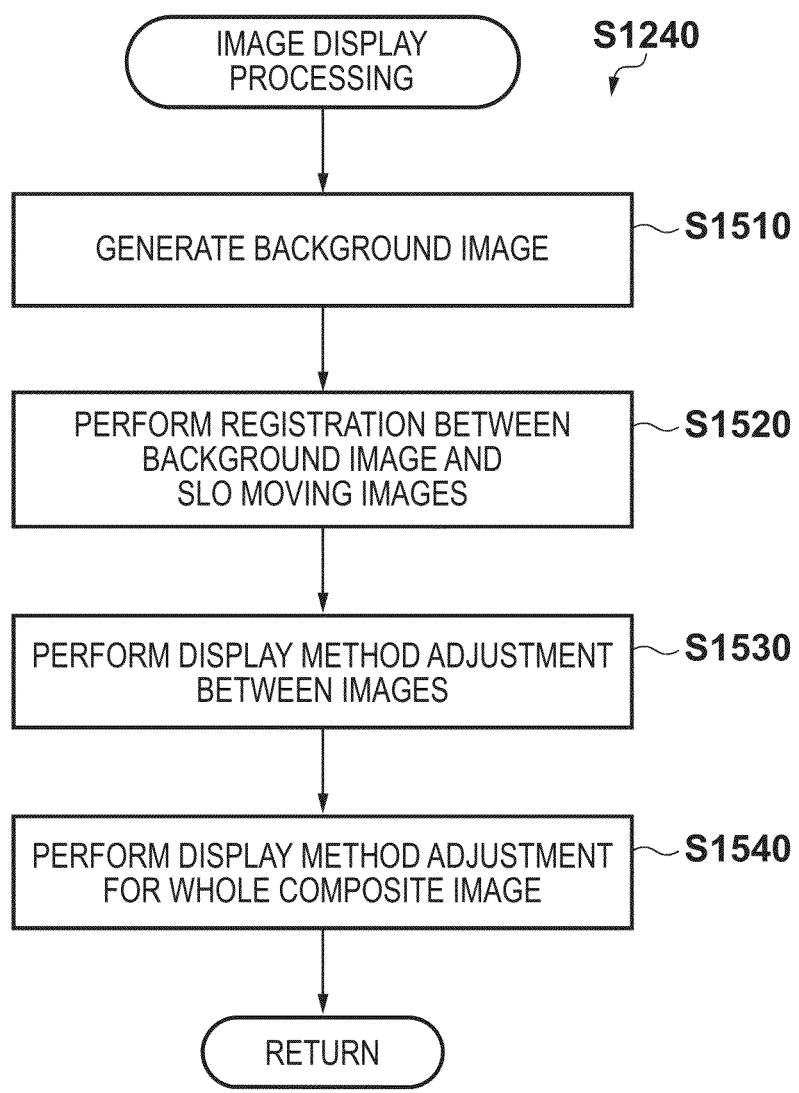

IMAGE DISPLAY APPARATUS, IMAGE DISPLAY METHOD AND IMAGING SYSTEM

TECHNICAL FIELD

The present invention relates to an image display apparatus, image display method, and imaging system, which are appropriate for ophthalmic care.

BACKGROUND ART

Examination of an eye portion is widely performed for the purpose of preemptive medical care for lifestyle-related diseases and other diseases occupying major causes of blindness. A scanning laser ophthalmoscope (SLO) serving as an ophthalmic apparatus based on the principle of a confocal laser microscope performs raster scan on a fundus with a laser beam serving as measurement light, and quickly obtains a high-resolution planar image based on the light intensity of a return beam. Such an apparatus for capturing a planar image will be referred to as an SLO apparatus hereinafter. The planar image will be referred to as an SLO image hereinafter.

In recent years, it has become possible to obtain an SLO image of a retina with an improved lateral resolution by increasing the beam size of measurement light in an SLO apparatus. As the beam size of measurement light increases, however, the resolution and SN ratio of a planar image decrease due to the aberration of an eye to be examined in obtaining an SLO image of a retina. To solve the problem, an adaptive optics SLO apparatus including an adaptive optics for causing a wavefront sensor to measure the aberration of an eye to be examined in real time, and causing a wavefront correction device to correct the aberration of measurement light and its return beam occurring at the eye to be examined has been developed. Such an adaptive optics SLO apparatus can obtain a high-lateral resolution SLO image.

For hemodynamics, it is useful to compare and observe the blood vessel diameters and blood cell speeds of the favorite site of vascular anomalies and another site (a normal site) for diagnosis and follow-up. Since retinal vessels have symmetry in the vertical direction with respect to an optic papilla, one of means for detecting early symptoms of an eye disease is to compare the blood vessel diameters and blood cell speeds of the upper and lower portions.

In the above comparison and observation operation, to fully understand the progress of a disease, it is important to identify the positional relationship with an anatomical site/lesion or a normal site outside the imaging area of a moving image. A wide field of view image is, therefore, additionally obtained for use in the comparison and observation operation (see Japanese Patent Laid-Open No. 2010-259543 (to be referred to as literature 1 hereinafter)). Note that the blood vessel diameter or blood flow velocity may change due to a normal vital reaction such as a cardiac cycle, motion, or a change in body temperature (in addition to a change caused by a disease). To compare images captured at different imaging positions, therefore, the images need to be captured under an almost equal influence of such a vital reaction. That is, it is necessary to obtain biomedical signal data (pulse data) such as a pulse wave in capturing images, and to respectively compare blood vessel diameters and blood flow velocities with each other at the cardiac end-diastole (when the blood vessel diameter is largest, and the blood flow velocity is lowest). To compare a plurality of moving images with different imaging positions, it is necessary to avoid the influence of eye/eyelid movement such as blinking or involuntary eye movement during fixation in addition to a change due to a vital reaction, and to correct differences in image features due to a difference in imaging conditions such as a difference in aberration correction position of an imaging apparatus.

As a method of synchronously displaying a plurality of moving images under an almost equal influence of the vital reaction of an object, a technique of simultaneously displaying a plurality of diagnosis images arranged in time-series according to the cardiac pulse is described in Japanese Patent Laid-Open No. 2011-005312 (to be referred to as literature 2 hereinafter).

Literature 2, however, describes only the technique of synchronously displaying a plurality of types of moving images of the same part or moving images with different imaging times of the same part, and does not describe a technique of associating the position of the images with that on a wide field of view image. The technique described in literature 2 is an analysis/display technique for an ultrasonic diagnostic apparatus, and does not consider display adjustment which should be taken into account to display an ophthalmology image, that is, the influence of blinking or involuntary eye movement during fixation, the aberration correction position of the imaging apparatus, and the like.

Literature 1 describes a technique of superimposing and displaying the imaging area of an adaptive optics SLO image on a wide range fundus image, which is, however, processing for a single SLO image, and does not consider a technique of performing display adjustment between SLO images with different imaging positions and different imaging times.

SUMMARY OF INVENTION

An embodiment of the present invention provides an image display apparatus for supporting appropriate diagnosis and a method therefor by enabling to readily compare and observe a plurality of moving images captured in a plurality of imaging areas of a fundus.

According to one aspect of the present invention, there is provided an image display apparatus comprising: image obtaining means for obtaining a plurality of moving images which are obtained by capturing a plurality of imaging areas of a fundus and each of which is associated with pulse data based on a biomedical signal obtained in capturing the moving image, and a wide field of view image obtained by capturing an area including the plurality of imaging areas of the fundus; display means for superimposing and displaying at least one frame of each of the plurality of moving images at a position on the wide field of view image, which is determined based on information about positions of the plurality of imaging areas; and a synchronous means for synchronizing, based on the pulse data, display timings of the plurality of moving images by the display means.

Furthermore, according to another aspect of the present invention, there is provided an image display method for an image display apparatus, comprising the steps of: obtaining a plurality of moving images which are obtained by capturing a plurality of imaging areas of a fundus and each of which is associated with pulse data based on a biomedical signal obtained in capturing the moving image, and a wide field of view image obtained by capturing an area including the plurality of imaging areas of the fundus; superimposing and displaying at least one frame of each of the plurality of moving images at a position on the wide field of view image, which is determined based on information about positions of the plurality of imaging areas; and synchronizing, based on the pulse data, display timings of the plurality of moving images in the step of superimposing and displaying.

Further features of the present invention will become apparent from the following description of exemplary embodiments with reference to the attached drawings.

BRIEF DESCRIPTION OF DRAWINGS

FIG. 6 is a flowchart illustrating processing executed in step S430 according to the first embodiment;

FIGS. 7A and 7B are views for explaining synchronization processing executed in step S430 according to the first embodiment;

FIGS. 10A to 10C are flowcharts illustrating processing executed in step S920 according to the second embodiment;

FIG. 15 is a flowchart illustrating processing executed in step S1240 according to the fourth embodiment.

DESCRIPTION OF EMBODIMENTS

Preferred embodiments of an image display apparatus and a method according to the present invention will be described in detail below with reference to the accompanying drawings. Note that the present invention is not limited to them.

[First Embodiment]

Based on pulse wave data, an image display apparatus according to the first embodiment synchronously displays a plurality of SLO moving images with different imaging positions at positions based on imaging position information on a wide field of view image. This synchronous display operation is performed under an almost equal influence of a fixation disparity, blinking, or an aberration correction failure in a plurality of SLO moving images.

More specifically, the image display apparatus captures a plurality of SLO moving images $Di$ ($i=1, 2, \ldots, n0$) at different imaging positions, and obtains pulse wave data $Pi$ ($i=1, 2, \ldots, n0$) in capturing the SLO moving images $Di$, respectively. After that, the image display apparatus determines, from each SLO moving image $Di$, exceptional frames where the influence of a fixation disparity, blinking, or the like has been exerted, and selects, based on extreme values of the corresponding pulse wave data $Pi$, a frame number sequence to be displayed from the SLO moving image $Di$. At this time, the apparatus selects a frame number sequence to be displayed so as to exclude the determined exceptional frames. The image display apparatus adjusts a playback speed between the SLO moving images $Di$ for the frame group of the selected frame number sequence, and synchronously displays the frame group on a wide field of view SLO image $W$ based on fixation target positions $Fi$ ($i=1, 2, \ldots, n0$) obtained in capturing the images. This processing enables to exert, on the SLO moving images $Di$, an almost equal influence of a variation in image characteristics due to a vital reaction such as pulsation or blinking, and a difference in imaging conditions such as a difference in aberration correction position. In addition, it is possible to compare and observe blood cell kinetics and a change in blood vessel shape between the SLO moving images $Di$ with different imaging positions and different imaging times while understanding the relationship with an anatomical site and the progress of a disease outside the imaging areas of the SLO moving images $Di$.

Figure 5B:
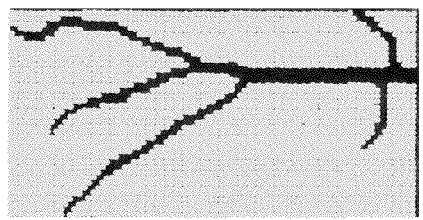
FIGS. 5A to 5E are views for explaining image display contents according to the first embodiment.
Figure 5C:
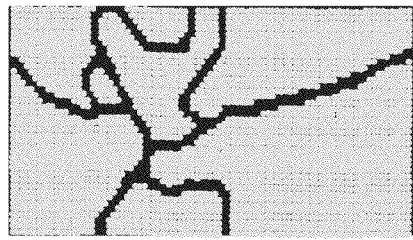
Figure 5E:
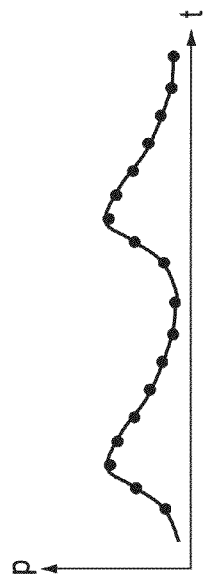
Figure 5A:
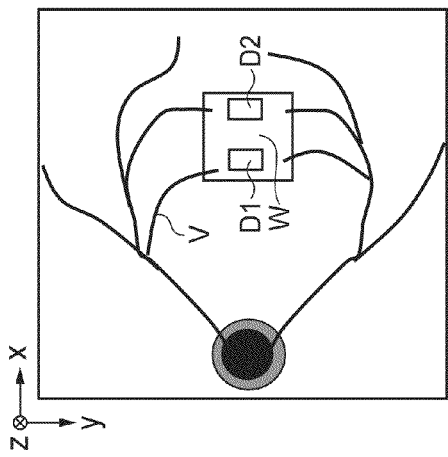
Figure 5D:
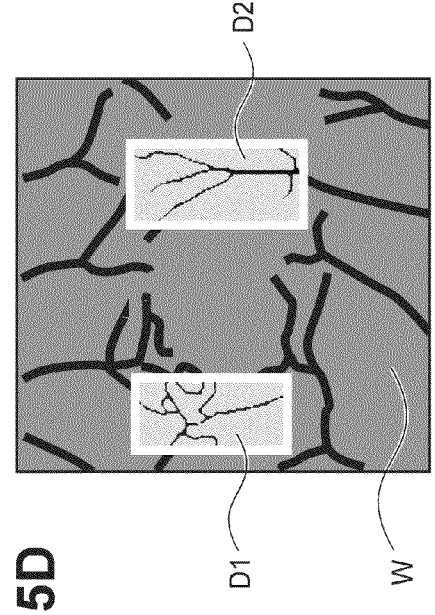

For example, FIGS. 5B and 5C show examples of planar images obtained by capturing areas of parafoveas $D1$ and $D2$ on a fundus shown in FIG. 5A. It is possible to obtain such a high-lateral resolution SLO image as a moving image (SLO moving image), which is used to measure a blood cell moving speed in a blood capillary after extracting retinal vessels and blood cells from each frame in order to noninvasively observe hemodynamics. Furthermore, to evaluate the relationship with the visual function from the planar images, photoreceptor cells may be detected, and then their density distribution and arrangement may be measured. In this embodiment, as shown in FIG. 5D, the SLO moving images $D1$ and $D2$ are synchronously displayed on the wide field of view SLO image $W$.

Figure 2:
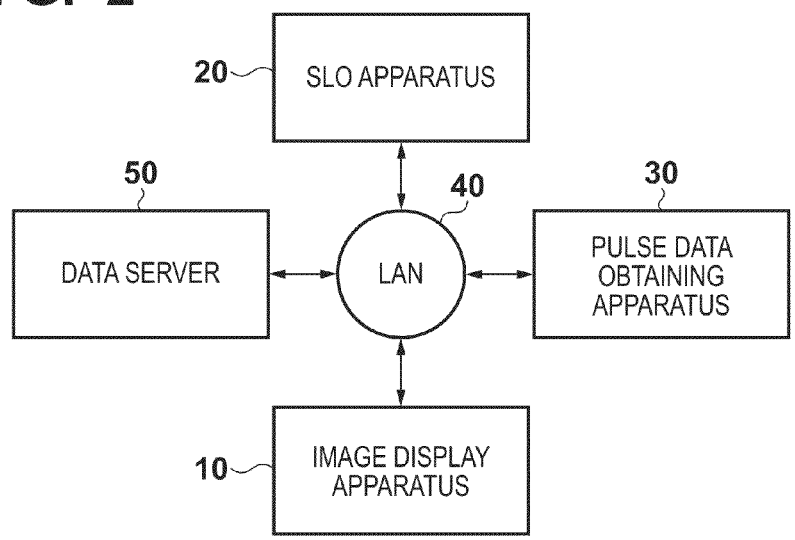
FIG. 2 is a block diagram showing an example of the configuration of an imaging system including the image display apparatus 10 according to the first embodiment.

FIG. 2 is a block diagram showing an example of the configuration of an imaging system including an image display apparatus 10 according to this embodiment. In the imaging system shown in FIG. 2, the image display apparatus 10 is connected with an SLO apparatus 20, a pulse data obtaining apparatus 30, and a data server 50 via a local area network (to be referred to as a LAN 40 hereinafter) formed by an optical fiber, a USB, IEEE1394, or the like. Note that the apparatus 10 may be connected with these apparatuses via an external network such as the Internet. One apparatus may implement some of the image display apparatus 10, SLO apparatus 20, pulse data obtaining apparatus 30, and data server 50. For example, one information processing apparatus may include the image display apparatus 10 and data server 50.

In FIG. 2, the SLO apparatus 20 serves as a scanning laser ophthalmoscope for capturing the planar image (SLO moving image) of a fundus region by scanning the fundus with a laser beam, and includes adaptive optics (to also be referred to as an aberration correction device). The SLO apparatus 20 captures the SLO moving images $Di$ at different imaging positions, and transmits, to the image display apparatus 10 and data server 50, via the LAN 40, the above-described SLO moving images $Di$ and information about fixation target positions $Fi$ used to capture them. The SLO apparatus 20 serving as an adaptive optics scanning laser ophthalmoscope (AO-SLO) includes an SLD, a Shack-Hartmann wavefront sensor, adaptive optics, first and second beam splitters, an X-Y scanning mirror, a focusing lens, an aperture stop, an optical sensor, an image forming unit, and an output unit. Light emitted by the SLD (Super Luminescent Diode) serving as a light source is reflected by the fundus. Some of the reflected light is incident on the Shack-Hartmann wavefront sensor through the second beam splitter, and the remaining light is incident on the optical sensor through the first beam splitter. The Shack-Hartmann wavefront sensor is a device for measuring aberration of an eye, and a CCD is connected to a lens array. When the incident light passes through the lens array, a luminescent spot group appears in the CCD, thereby measuring wave aberration based on misregistration of the projected luminescent spots. Based on the wave aberration measured by the Shack-Hartmann wavefront sensor, the adaptive optics drives the aberration correction device (a deformable mirror or spatial light phase modulator) to correct aberration. The light having undergone the aberration correction enters the optical sensor through the focusing lens and aperture stop. It is possible to control a scanning position on the fundus by moving the X-Y scanning mirror, thereby obtaining data for a time (frame rate×number of frames) and an imaging target area designated in advance by an operator. The data is transmitted to the image forming unit, which forms image data (a moving image or still image) by correcting image distortion due to a variation in scanning speed or correcting luminance values. The output unit outputs the image data formed by the image forming unit. To focus on a specific depth position on the fundus, it is possible to perform at least one of adjustment using the aberration correction device of the adaptive optics and adjustment by arranging a focus adjustment lens (not shown) in the optics and moving the lens. Note that it is possible to use an ophthalmic apparatus such as a fundus camera including adaptive optics or an aberration correction device, instead of the SLO apparatus 20.

The pulse data obtaining apparatus 30 is used to obtain biomedical signal data (pulse data) which autonomously changes, and includes, for example, a sphygmograph or electrocardiograph. In this embodiment, since pulse wave data are used as pulse data, the above-described pulse wave data Pi are described as pulse data Pi. In response to an operation by an operator (not shown), the pulse data obtaining apparatus 30 obtains pulse data Pi as well as the SLO moving images Di. The obtained pulse data Pi are transmitted to the image display apparatus 10 and data server 50 via the LAN 40.

Figure 4:
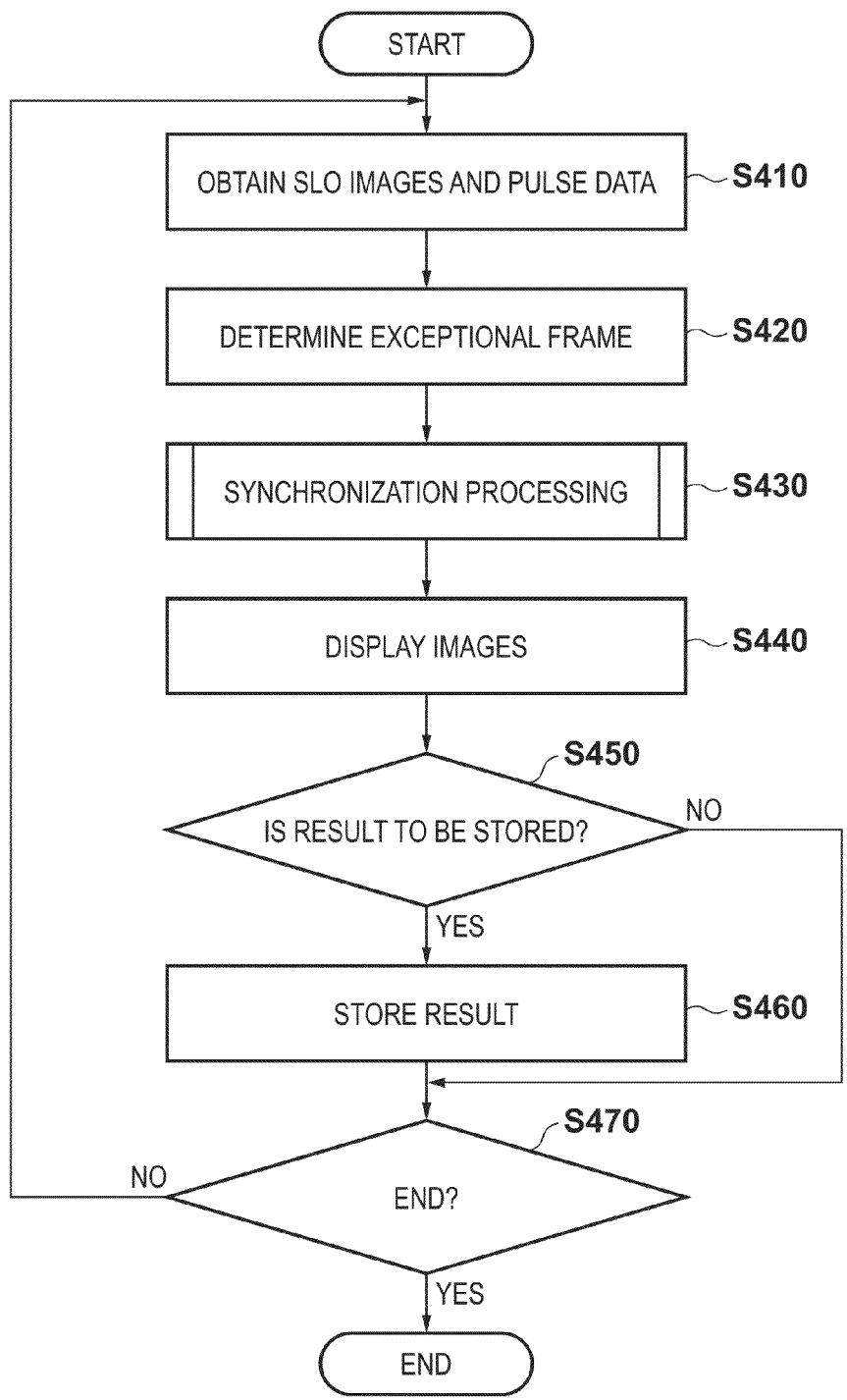
FIG. 4 is a flowchart illustrating processing executed by the image display apparatus 10 according to the first embodiment.

The data server 50 holds the SLO moving images Di of the eye to be examined, imaging condition data such as the fixation target positions Fi, the pulse data Pi, and information from the image display apparatus 10. That is, the data server 50 stores the wide field of view image W, SLO moving images Di and fixation target positions Fi output from the SLO apparatus 20, the pulse data Pi output from the pulse data obtaining apparatus 30, and the information output from the image display apparatus 10 (step S460 in FIG. 4). Furthermore, in response to a request from the image display apparatus 10, the data server 50 transmits the wide field of view image W, the SLO moving images Di, the pulse data Pi, the image features of the eye portion, and the normal value data of the image features to the image display apparatus 10 via the LAN 40. Although an arrangement in which the image display apparatus 10 obtains the SLO moving images and pulse data from the SLO apparatus 20 and pulse data obtaining apparatus 30, and executes image display processing will be described below, the present invention is not limited to this. It is apparent that, for example, the image display apparatus 10 may obtain the SLO images and the pulse data associated with them stored in the data server 50, and execute image display processing to be described below.

Figure 3:
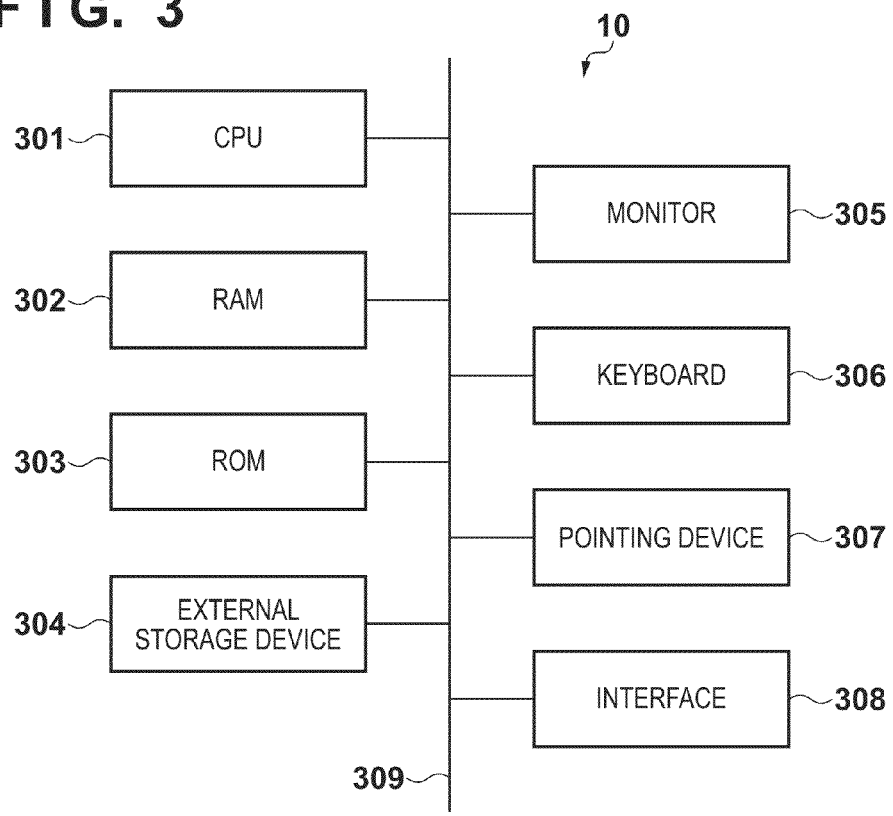
FIG. 3 is a block diagram showing an example of the hardware arrangement of a computer capable of executing an image display method according to the embodiment.

The hardware arrangement of the image display apparatus 10 will be described with reference to FIG. 3. Referring to FIG. 3, reference numeral 301 denotes a central processing unit (to be referred to as the CPU 301); 302, a readable/writable memory (to be referred to as the RAM 302); 303, a control memory (to be referred to as the ROM 303); and 304, an external storage device. Furthermore, referring to FIG. 3, reference numeral 305 denotes a monitor; 306, a keyboard; 307, a pointing device (for example, a mouse); and 308, an interface. The above respective units are communicably connected with each other via a bus 309. The external storage device 304 stores control programs for implementing an image processing function according to the embodiment, and data to be used to execute the control programs. The control programs and data are loaded, as needed, into the RAM 302 via the bus 309 under the control of the CPU 301, and executed by the CPU 301, thereby functioning as each unit to be explained below with reference to FIG. 1.

Figure 1:
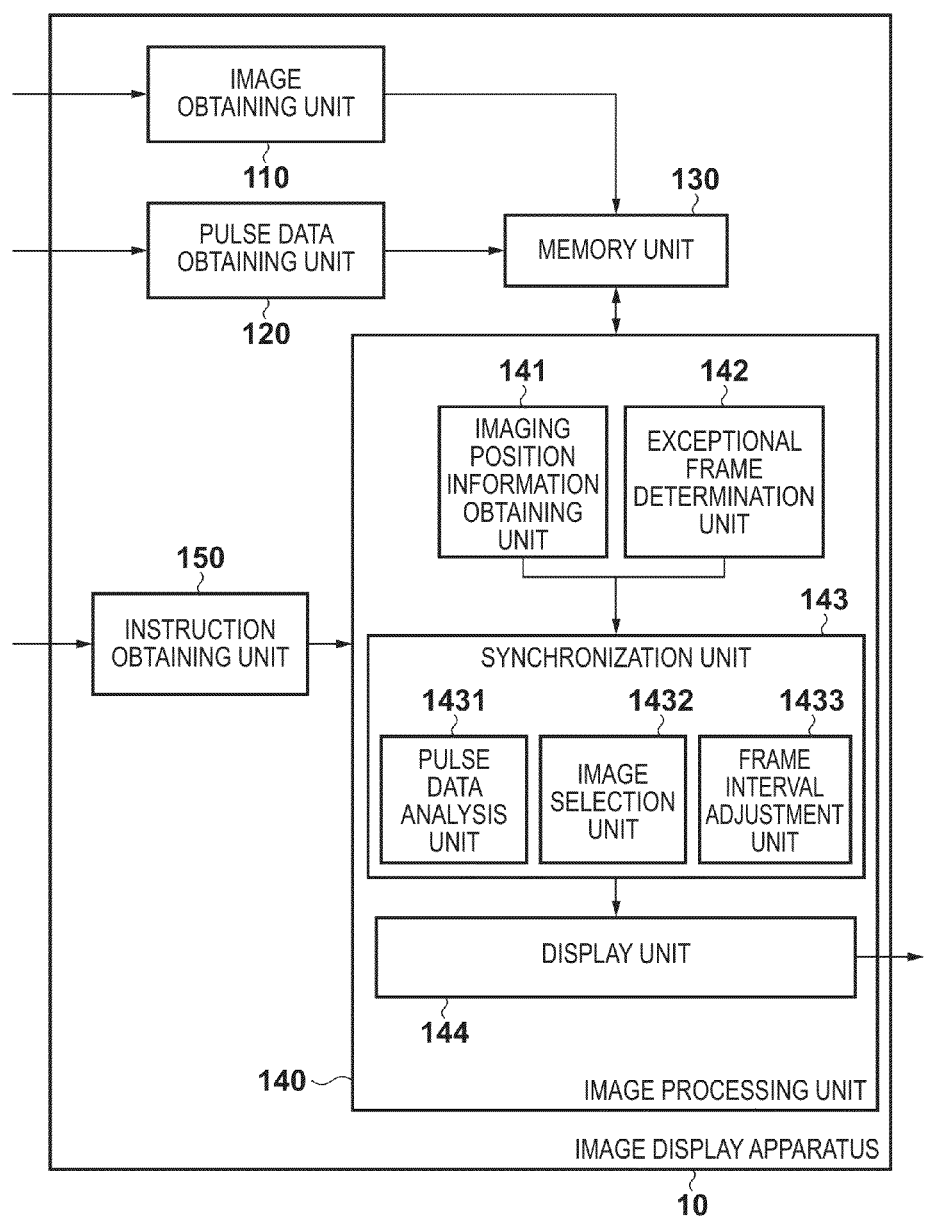
FIG. 1 is a block diagram showing an example of the functional arrangement of an image display apparatus 10 according to the first embodiment.

The functional arrangement of the image display apparatus 10 according to the embodiment will now be described with reference to FIG. 1. FIG. 1 is a block diagram showing the functional arrangement of the image display apparatus 10 according to the first embodiment. The image display apparatus 10 includes an image obtaining unit 110, a pulse data obtaining unit 120, a memory unit 130, an image processing unit 140, and an instruction obtaining unit 150. The image processing unit 140 includes an imaging position information obtaining unit 141, an exceptional frame determination unit 142, a synchronization unit 143, and a display unit 144. The synchronization unit 143 includes a pulse data analysis unit 1431, an image selection unit 1432, and a frame interval adjustment unit 1433. The function of each block of the image display apparatus 10 will be described below in association with the practical execution procedure of the image display apparatus 10 shown in the flowchart of FIG. 4.

<Step S410> The image obtaining unit 110 and pulse data obtaining unit 120 obtain a plurality of moving images (SLO moving images) obtained by capturing a plurality of imaging areas of a fundus, and a wide field of view image obtained by capturing an area including the plurality of areas. Note that the plurality of moving images are stored in the memory unit 130 in association with pulse data based on biomedical signals respectively obtained in capturing the images. More specifically, the pulse data obtaining unit 120 requests the pulse data obtaining apparatus 30 to obtain pulse data Pi associated with the biomedical signals. In this embodiment, a plethysmograph is used as the pulse data obtaining apparatus 30 to obtain pulse wave data as the pulse data Pi from an ear lobe of an object. Note that the pulse data Pi is represented as a sequence of points having the abscissa indicating an obtaining time (t) and the ordinate indicating a pulse wave signal value (p) measured by the plethysmograph, as shown in FIG. 5E. In response to the obtaining request from the pulse data obtaining unit 120, the pulse data obtaining apparatus 30 obtains the corresponding pulse data Pi and transmits it. The pulse data obtaining unit 120 then receives the pulse wave data Pi from the pulse data obtaining apparatus 30 via the LAN 40. The pulse data obtaining unit 120 stores the received pulse data Pi in the memory unit 130.

Simultaneously with the processing of obtaining the pulse data, the image obtaining unit 110 requests the SLO apparatus 20 to obtain a wide field of view SLO image (to be referred to as a wide field of view image W), a plurality of SLO moving images Di with different imaging positions, which have been captured at a plurality of different fixation target positions Fi, and data of the fixation target positions Fi. In this embodiment, the SLO apparatus 20 sequentially obtains the SLO moving images Di (D1 to D4) by setting the fixation target positions at four positions, that is, the nose side (F1), ear side (F2), upper side (F3), and lower side (F4) in the parafovea and the wide field of view image W of a macular region. Note that the imaging position setting method is not limited to this, and imaging positions may be set at arbitrary positions.

To associate the SLO moving images with the pulse data based on the biomedical signals obtained in capturing them, respectively, the image obtaining unit 110 may start obtaining the SLO moving images Di according to a given phase of the pulse data Pi obtained by the pulse data obtaining apparatus 30, or the image obtaining unit 110 may start obtaining the pulse wave data Pi and SLO moving images Di at the same time immediately after the request to obtain the SLO moving images Di is sent. Assume, in this embodiment, that the image obtaining unit 110 starts obtaining the pulse data Pi and SLO moving images Di immediately after the request to obtain the SLO moving images Di is sent.

In response to the obtaining request from the image obtaining unit 110, the SLO apparatus 20 obtains the wide field of view SLO image (to be referred to as the wide field of view image W hereinafter), the SLO moving images Di, and the fixation target positions Fi to transmit them. The image obtaining unit 110 receives the wide field of view image W, the SLO moving images Di, and the fixation target positions Fi from the SLO apparatus 20 via the LAN 40. The image obtaining unit 110 stores the received wide field of view image W, SLO moving images D, and fixation target positions Fi in the memory unit 130. Note that in this embodiment, the received SLO moving images Di are moving images having undergone inter-frame registration. The inter-frame registration indicates adjustment such that the images of adjacent frames are at the same position, and is implemented by a well-known technique. The SLO apparatus 20 includes an aberration correction device, and outputs the SLO moving images Di having undergone aberration correction. Note that the aberration correction device need not perform aberration correction for the wide field of view image W since it does not require a high resolution with compared with the SLO moving images of the respective positions.

<Step S420> The exceptional frame determination unit 142 obtains image features from each frame of the SLO moving image Di, and determines exceptional frames of the plurality of frames of the SLO moving image Di. In this embodiment, the exceptional frame determination unit 142 obtains an average luminance value Aij and a blood vessel area Vij as image features in each frame j (j=1, 2, . . . , n1) of the SLO moving image Di. Note that the mentioned image features are merely examples, and the present invention is not limited to them. Note also that an arbitrary known blood vessel extraction method can be used as a blood vessel area obtaining method. In this embodiment, an area with a luminance value equal to or smaller than a threshold T1 is determined as a blood vessel area. Furthermore, intersection portions Cijl (l=1, . . . , n3) of a sequence of points Bijk (k=1, 2, . . . , n2) obtained by thinning the blood vessel area Vj are also obtained.

The unit 142 detects, from each SLO moving image Di, an exceptional frame, that is, a frame where the luminance is extremely low due to blinking, a frame where image distortion has occurred due to involuntary eye movement during fixation, or a frame where an SN ratio (signal to noise ratio) is low due to an aberration correction failure. In this embodiment, if the average luminance value Aij is equal to or smaller than a threshold T2 , the frame j of the SLO moving image Di is considered as a frame where a luminance error has occurred due to blinking, thereby determining it as an exceptional frame. If the difference, between adjacent frames, in value of the sum of squares of the distance between the blood vessel intersection portions Cijl is equal to or larger than a threshold T3, it is considered that image distortion has occurred due to involuntary eye movement during fixation, thereby determining the frame as an exceptional frame. Furthermore, if the SN ratio is equal to or smaller than a threshold T4, it is considered that an aberration correction failure has occurred, thereby determining the frame as an exceptional frame.

<Step S430> The synchronization unit 143 executes processing for synchronizing the playback timings of the respective moving images based on the pulse data in playback/display processing of the plurality of SLO moving images in step S440 (to be described later). The synchronization unit 143 obtains the pulse data Pi of each SLO moving image Di from the pulse data obtaining unit 120, and detects the local maximum values of the pulse data Pi to calculate a cardiac cycle. The synchronization unit 143 then obtains an exceptional frame number sequence detected in step S420 for each SLO moving image Di. The synchronization unit 143 selects a frame to be displayed so as to exclude the exceptional frames. Furthermore, if there is a difference in cardiac cycle of the selected frame between the SLO moving images Di, the synchronization unit 143 adjusts a display frame interval between the SLO moving images Di. The processing by the synchronization unit 143 will be described in detail later with reference to FIGS. 6, 7A and 7B.

<Step S440> The display unit 144 superimposes and displays the plurality of SLO moving images at positions, on the wide field of view image W, based on information about the positions of the plurality of imaging areas. In the first embodiment, fixation target positions are used as the information about the positions of the imaging areas. That is, at the playback timing determined by the synchronization unit 143, the display unit 144 synchronously displays the SLO moving images Di with different imaging positions at positions, on the wide field of view image W, corresponding to the fixation target positions Fi obtained by the imaging position information obtaining unit 141. The moving images Di with different imaging positions are not simply arranged in synchronism with each other with respect to a pulse wave but superimposed and displayed at corresponding parts on the wide field of view image W. This helps the operator as an observer (a doctor and the like) identify a lesion outside the imaging areas of the SLO moving images Di or the positional relationship between the imaging areas and anatomical sites, thereby enabling the observer to more readily and fully understand the progress of a disease on the SLO moving images Di.

Note that the image display method is not limited to this, and an arbitrary display method may be used. For example, a known feature extraction method is used to detect a specific area such as a blood vessel area Vi or a lesion area from the SLO moving images Di, and only the specific area such as the blood vessel area Vi or the lesion area may be synchronously displayed on the wide field of view image W.

<Step S450> The instruction obtaining unit 150 obtains an instruction indicating whether to store, in the data server 50, the wide field of view image W and SLO moving images Di displayed in step S440, the fixation target positions Fi, the exceptional frame number sequence, and the analysis data (extreme values and cycle) of the pulse wave. The operator inputs the instruction via, for example, the keyboard 306 or pointing device 307. If a storage operation is instructed, the process advances to step S460; otherwise, the process advances to step S470.

<Step S460> The image processing unit 140 transmits, to the data server 50, an examination date/time, information for identifying an eye to be examined, the wide field of view image W, the SLO moving images Di, the fixation target positions Fi of the image group, the exceptional frame number sequence, and the analysis data of the pulse wave in association with each other.

<Step S470> The instruction obtaining unit 150 obtains an instruction indicating whether to terminate the display processing of the SLO moving images by the image display apparatus 10. The operator inputs the instruction via the keyboard 306 or pointing device 307. If the unit 150 obtains an instruction to terminate the processing, the analysis processing ends. On the other hand, if the unit 150 obtains an instruction to continue the processing, the process returns to step S410 to execute processing for a next eye to be examined (or re-execute processing for the same eye to be examined).

The synchronization processing executed in step S430 will be described in detail with reference to FIGS. 6, 7A, and 7B. The synchronization processing selects display target sections from the plurality of respective SLO moving images so as to limit the number of exceptional frames to be played back (set the number of exceptional frames to be played back to be equal to or smaller than a predetermined number (including 0)), and synchronously displays the selected sections.

<Step S610> The pulse data analysis unit 1431 obtains the pulse data Pi of each SLO moving image Di from the pulse data obtaining unit 120, and detects the local maximum values of the pulse data Pi to calculate a cardiac cycle. In this embodiment, a time interval between adjacent local maximum values or local minimum values in the pulse data is set as a cardiac cycle.

<Step S620> The synchronization unit 143 obtains the exceptional frame number sequence of the SLO moving image Di determined by the exceptional frame determination unit 142 in step S420.

<Step S630> The image selection unit 1432 selects, from the SLO moving image Di, a frame number sequence to be displayed by the display unit 144 so that the number of exceptional frames is as small as possible.

A practical frame selection method in step S630 will be described with reference to FIG. 7A. Referring to FIG. 7A, the SLO moving images D1 to D4 have been obtained at the different fixation target positions F1 to F4. In each SLO moving image Di, a white portion represents a normal frame sequence (Dioi) including continuous frames without any exceptional frame, and a gray portion (hatched portion) represents an exceptional frame sequence (Eipi). Furthermore, for the SLO moving images Di (D1 to D4 ), the imaging periods are equal to each other but the phases of the pulse data Pi in respective start frames are different from each other. In this embodiment, one normal frame sequence is selected from each of D1o1 (o1=1, 2), D2o2 (o2=1, 2), D3o3 (o3=1), and D4o4 (o4=1, 2) is selected, thereby obtaining a common pulse section length. A frame number sequence included in a pulse section C1 with a maximum section length of the common pulse is selected from each of the SLO moving images Di (D1 to D4). That is, a section, the pulse of which is common to all the SLO moving images and in which normal frames continue (no exceptional frame is included), is set as a common section, and a common section with a longest length is selected. The display unit 144 synchronously displays frames corresponding to the selected common section of each SLO moving image. Note that the cardiac cycle is not strictly constant in obtaining each SLO moving image Di. Therefore, the cardiac cycles are normalized, and the SLO moving images Di are arranged so that the common pulse section length becomes long.

Note that the display frame selection method is not limited to this, and an arbitrary selection method may be used. For example, a longest section in each pulse cycle may be selected. In the example of FIG. 7A, a longest section C2 with a length of one cycle has been selected. Alternatively, a tolerance T5 (1 in this example) of the number of exceptional frame sequences may be set, and a frame number sequence included in a longest pulse section, obtained by extending the pulse section C1, in which the number of exceptional frame sequences is equal to or smaller than the tolerance T5 may be selected from each of the SLO moving images Di (D1 to D4). For example, FIG. 7A shows a case in which a longest pulse section C3 has been selected when T5=1.

<Step S640> The frame interval adjustment unit 1433 adds or deletes frames so that at least the numbers of frames of the respective SLO moving images in a section to be synchronously played back are almost equal to each other. In this embodiment, the following processing is executed so that the numbers of frames in each cycle indicated by the pulse data are equal to each other. The frame interval adjustment unit 1433 obtains a cardiac cycle Hi in a frame number sequence Ii which has been selected from each SLO moving image Di in step S640. The cardiac cycle Hi may generally change depending on the SLO moving image Di, and also change within the same SLO moving image as shown in FIG. 7B. In this embodiment, a cardiac cycle Hr (1.0 [sec] in FIG. 7B) closest to a normal cycle is set as a reference cycle. If the difference between a given cycle and the reference cycle Hr is equal to or larger than a tolerance T6, the cycle is considered as a different one, and then the process advances to step S650. If the difference between a given cycle and the reference cycle Hr is smaller than the tolerance T6, the synchronization processing ends, and the process advances to step S440.

Note that the method of setting the reference cycle Hr is not limited to this, and an arbitrary setting method may be used. For example, a general normal value (1.0 [sec]) may be simply set as a reference cycle, or a relatively large value (5.0 [sec]) which is readily visually recognizable may be set as a reference cycle. Alternatively, instead of a single value, a tolerance range (for example, 0.9 to 1.1 [sec]) may be set.

<Step S650> If the difference between the reference cycle Hr and the cardiac cycle Hi of the pulse data corresponding to the frame number sequence Ii is equal to or larger than the tolerance T6, the frame interval adjustment unit 1433 executes processing of adjusting the interval of frames to be played back (step S650). In this embodiment, as a practical playback frame interval adjustment method, if Hi<Hr, a frame generated by performing interpolation processing from the preceding and subsequent frames is inserted, and if Hi>Hr, the number of frames is reduced.

By executing the processing, the frame interval is adjusted so that the cardiac cycle Hi becomes almost equal to the reference cycle Hr.

If, for example, a section 710 of an SLO moving image of FIG. 7B is selected as display frames, a section 711 has a cardiac cycle (0.9 sec) shorter than the reference cycle Hr (1 sec), and a section 712 has a cardiac cycle (1.1 sec) longer than the reference cycle Hr. In this case, in the section 711, one frame is generated and inserted by the interpolation processing every 10 frames. In the section 712, one frame is deleted every 11 frames.

In this embodiment, the wide field of view image W is a still image, and the exceptional frame determination processing executed in step S420 and the synchronization processing executed in step S430 are performed for the SLO moving images Di. The present invention, however, is not limited to this. For example, the wide field of view image W may be a moving image, exceptional frame determination processing similar to that in step S420 may also be executed for the wide field of view image W, and then the synchronization processing may be executed between the wide field of view image W and the SLO moving images Di.

As described above, the image display apparatus 10 according to the first embodiment synchronizes the plurality of SLO moving images Di with different imaging positions based on the pulse data Pi, and superimposes and displays them at positions based on fixation target position information on the wide field of view image. At this time, a frame including a fixation disparity or blinking, or a frame with a low SN ratio is excluded from display targets. This makes it possible to observe blood cell kinetics and a change in blood vessel shape between the SLO moving images Di with different imaging positions under the almost equal influence of differences in image features due to a difference in imaging conditions and a vital reaction such as pulsation or blinking. It is, therefore, possible to compare and observe the plurality of SLO moving images Di while understanding the relationship with an anatomical site and the progress of a disease outside the imaging areas of the moving images.

[Second Embodiment]

In the first embodiment, the SLO moving images Di are arranged on the wide field of view image based on the fixation target positions Fi. In the second embodiment, an arrangement in which SLO moving images are more correctly arranged on a wide field of view image W based on registration parameters obtained by a registration unit 145 (FIG. 8) will be described.

According to the second embodiment, therefore, it is possible to correctly determine positions on the wide field of view image W even if SLO moving images Di are shifted from fixation target positions Fi to some extent due to involuntary eye movement during fixation. Even if there are differences in image features due to a vital reaction such as pulsation, blinking, or a fixation disparity, or a difference in imaging conditions such as a difference in aberration correction position, it is possible to readily compare and observe blood cell kinetics and a change in blood vessel shape between the SLO moving images Di with different imaging positions.

Figure 8:
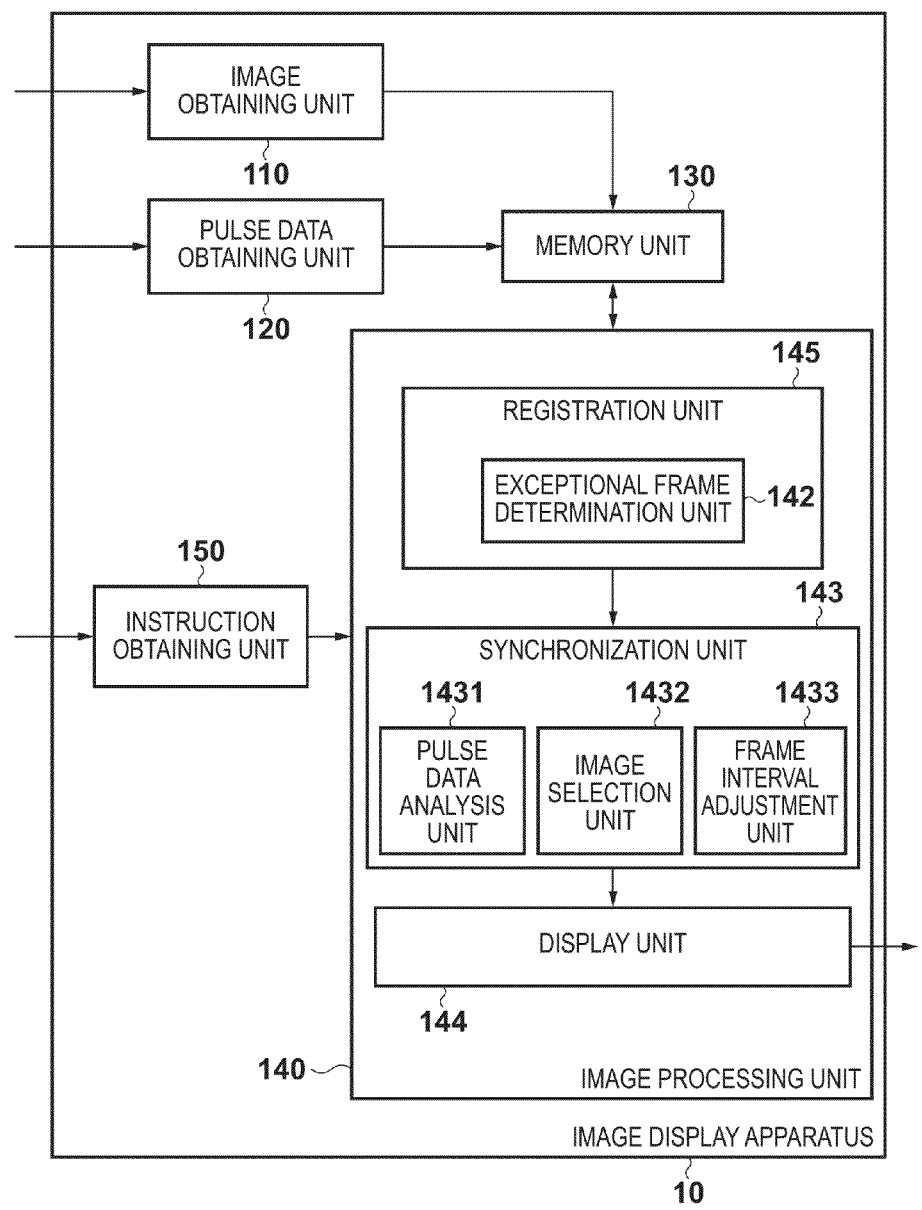
FIG. 8 is a block diagram showing an example of the functional arrangement of an image display apparatus 10 according to the second embodiment.
Figure 9:
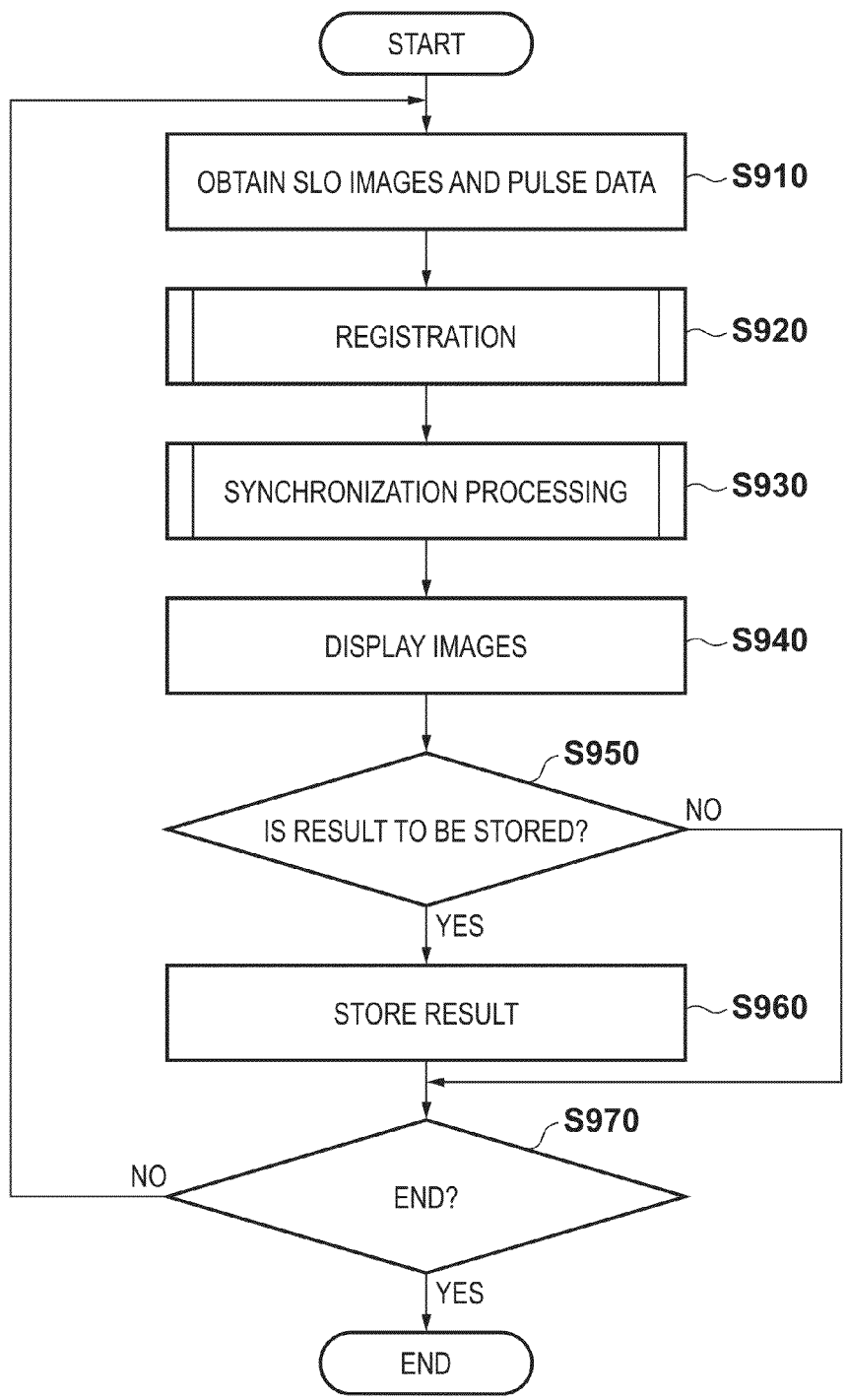
FIG. 9 is a flowchart illustrating processing executed by the image display apparatus 10 according to the second embodiment.

FIG. 8 is a functional block diagram showing an image display apparatus 10 according to the second embodiment. The image display apparatus 10 according to the second embodiment is provided with the registration unit 145 instead of the imaging position information obtaining unit 141 of the first embodiment, and the registration unit 145 includes an exceptional frame determination unit 142. FIG. 9 shows an image display procedure according to the second embodiment. Steps except for step S920 are the same as those in the first embodiment (steps S910 and S930 to S970 of FIG. 9 correspond to steps S410 and S430 to S470 of FIG. 4, respectively). Processing in step S920 will be described below.

<Step S920> The registration unit 145 reads the wide field of view image W and the plurality of SLO moving images Di with different imaging positions from a memory unit 130 to (i) perform inter-frame registration for each SLO moving image Di, and (ii) perform registration between the wide field of view image W and the SLO moving image Di.

The processing executed in step S920 will be described in more detail below with reference to a flowchart shown in FIG. 10A.

<Step S1010> The registration unit 145 sets a reference frame as a reference for registration in the SLO moving image Di, and performs rough registration (coarse registration) using affine transformation. The registration unit 145 also performs non-rigid registration as fine registration. Note that in step S1010, the exceptional frame determination unit 142 detects an exceptional frame including a luminance error, image distortion, low SN ratio, or frame out from the SLO moving image Di. The above-described inter-frame registration processing is executed for all the SLO moving images Di. In this embodiment, an exceptional frame is determined using the image features of a single frame before inter-frame registration, and then inter-frame registration is performed for frames except for the exceptional frames. After that, for the frames having undergone the inter-frame registration, exceptional frame determination is performed based on differences in image features between the frames. As described above, exceptional frames are not used in inter-frame registration, and it is thus possible to perform inter-frame registration more efficiently and correctly. This processing will be described in more detail later with reference to a flowchart shown in FIG. 10B. Furthermore, since exceptional frame determination is performed based on the difference between frames using moving images having undergone inter-frame registration, it is possible to determine an exceptional frame with higher accuracy.

<Step S1020> The registration unit 145 performs registration for each SLO moving image Di with respect to the wide field of view image W. The registration unit 145 calculates the inter-image similarity between the wide field of view image W and each SLO moving image Di while changing registration parameters, and determines the relative position of the SLO moving image Di with respect to the wide field of view image W using registration parameters with which a highest inter-image similarity is obtained. This processing will be described in more detail later with reference to a flowchart shown in FIG. 10C.

The inter-frame registration processing executed in step S1010 will now be described in detail with reference to the flowchart shown in FIG. 10B.

<Step S1011> The exceptional frame determination unit 142 performs exceptional frame determination using a single frame for each frame of each SLO moving image Di. In this embodiment, the exceptional frame determination unit 142 calculates an average luminance value Aij and SN ratio SNj of each frame. If the average luminance value Aij is equal to or smaller than a threshold T2 or the SN ratio SNj is equal to or smaller than a threshold T4, it is considered that a luminance error has occurred or that the frame has low image quality, thereby determining the frame as an exceptional frame.

Note that the method of determining an exceptional frame using a single frame is not limited to this, and an arbitrary exception determination method may be used. For example, the luminance statistic (average value, mode, or maximum value) of a differential image obtained by executing differential processing for each frame is calculated. If the luminance statistic is equal to or smaller than a threshold T7, it may be considered that the frame blurs due to movement of an object, thereby determining it as an exceptional frame.

<Step S1012> The registration unit 145 sets a reference frame as a reference for registration. In this embodiment, the unit 145 sets, as a reference frame, a frame with a smallest frame number among frames other than those which have been determined as exceptional frames in step S1011. Note that the reference frame setting method is not limited to this, and an arbitrary setting method may be used. For example, the unit 145 may obtain a reference frame number designated by the user from the instruction obtaining unit 150, and set a frame with the reference frame number as a reference frame.

<Step S1013> The registration unit 145 roughly associates positions of frames with each other (coarse registration). Although an arbitrary registration method can be used for the coarse registration, the coarse registration is performed using a correlation coefficient as an inter-image similarity evaluation function and using affine transformation as a coordinate transformation method in this embodiment.

<Step S1014> The registration unit 145 performs fine registration based on data of the coarse positional correspondence between frames obtained in step S1013. In this embodiment, the unit 145 performs fine registration between frames using an FFD (Free Form Deformation) method as a non-rigid registration method for a moving image Dic which has undergone coarse registration in step S1013. Note that the fine registration method is not limited to this, and an arbitrary registration method may be used.

<Step S1015> The exceptional frame determination unit 142 performs exceptional frame determination for each frame of the moving image Dif which has undergone fine registration in step S1014. In this embodiment, the exceptional frame determination unit 142 calculates a difference between the reference frame and each frame (except for the reference frame), thereby obtaining the histogram of a difference image. If the average value of the histogram is equal to or larger than a threshold T8 and the variance of the histogram is equal to or larger than a threshold T9, the exceptional frame determination unit 142 considers that a different position on the fundus is temporarily captured due to involuntary eye movement during fixation, that is, a movement amount between the frames exceeds a predetermined value, thereby determining the frame as an exceptional frame.

Note that the exceptional frame determination method using differences in image features between frames in step S1015 is not limited to this, and an arbitrary determination method may be used. For example, for each frame of the moving image Dif having undergone fine registration, extraction of blood vessels and detection of blood vessel intersection portions Cijl are performed as in the first embodiment. The sum of squares of the distance between the blood vessel intersection portions Cijl is obtained in each frame. If the difference in value of the sum of squares of the distance between adjacent frames is equal to or larger than a threshold T3, it is considered that image distortion has occurred, thereby determining the frame as an exceptional frame.

The processing of performing registration between the wide field of view image and each moving image, which is executed in step S1020, will be described in detail with reference to a flowchart shown in FIG. 10C.

<Step S1021> The registration unit 145 obtains the fixation target position Fi used to capture the SLO moving image Di from the memory unit 130, and sets it as the search initial point of registration parameters in registration between the wide field of view image W and the SLO moving image Di. In this embodiment, translation (x and y), rotation θ, and a magnification s are obtained as registration parameters. The initial values of the parameters are set as follows.

$(x0, y0, \theta 0, s0) = (x$ component of $Fi, y$ component of $Fi, 0,$ (pixel size of wide field of view image/pixel size of moving image $Di$))

<Step S1022> The registration unit 145 uses, as the initial values, a combination of registration parameter values (x0, y0, θ0, s0) set in step S1021 to perform registration between the wide field of view image W and the SLO moving image Di while changing the combination of the parameter values.

Note that in this embodiment, the wide field of view image W is a still image, and a combination of registration parameter values with which the inter-image similarity between the wide field of view image W and the reference frame of the SLO moving image Di is highest is adopted as the relative position of the SLO moving image Di with respect to the wide field of view image W. Note also that the registration method is not limited to this, and an arbitrary registration method may be used.

In this embodiment, inter-frame registration is performed for the SLO moving image Di using pixel value-based inter-image similarity, thereby obtaining, as a relative position on the wide field of view image W, a combination of registration parameters with which the reference frame is most similar to the wide field of view image W. The present invention, however, is not limited to this. For example, image features (a part such as a lesion and central fovea, and a feature point such as a branch of a blood vessel) to be observed may be detected from each frame of the SLO moving image Di or the wide field of view image W, and registration between frames of the SLO moving image Di or between the wide field of view image W and the SLO moving image Di may be performed so that the positions of the image features most finely coincide with each other.

In this embodiment, the wide field of view image W is a still image, and registration between the wide field of view image W and the reference frame of the SLO moving image Di is performed. The present invention, however, is not limited to this. For example, the wide field of view image W may be a moving image, and registration between the wide field of view image W and the SLO moving image Di may be performed. In this case, for example, the following processing may be executed.

In step S920, inter-frame registration is performed for all the moving images including the wide field of view image W.

In step S930, synchronization processing as described in the first embodiment is executed.

A combination of registration parameters with which the inter-image similarity between a frame j of the wide field of view image W and a corresponding frame Dij of the SLO moving image Di is highest is obtained. This operation is performed for each frame of the wide field of view image W, thereby determining a relative position on the wide field of view image W.

As described above, according to the second embodiment, for each SLO moving image, the image display apparatus 10 eliminates the influence by a fixation disparity, blinking, or an aberration correction failure before and after inter-frame registration, and then superimposes and displays the SLO moving image on the wide field of view image W. This makes it possible to display blood cell kinetics and a change in blood vessel shape between the SLO moving images Di with different imaging positions under an almost equal influence of differences in image features due to a difference in imaging conditions and a vital reaction such as pulsation or blinking. The observer can, therefore, compare and observe the moving images while understanding the relationship with an anatomical site and the progress of a disease outside the imaging areas of the moving images. Note that a frame including a fixation disparity or blinking or a frame with low image quality of the SLO moving image Di may be determined as an exceptional frame using image features obtained in inter-frame registration. Alternatively, inter-frame registration may be performed using the image features obtained in the exceptional frame determination. In this way, commonly using image features in the inter-frame registration operation and the exceptional frame determination operation can improve the processing efficiency.

[Third Embodiment]

In the third embodiment, in addition to the arrangement of the second embodiment, a display unit 144 adjusts the luminance between SLO moving images Di with different imaging positions and/or between a wide field of view image W and each SLO moving image Di. This operation also adjusts not only the positional relationship and display timing but also the luminance characteristics between the SLO moving images Di with different imaging positions or between the wide field of view image W and each SLO moving image Di. The observer can, therefore, more readily compare and observe blood cell kinetics and a change in blood vessel shape.

Figure 11:
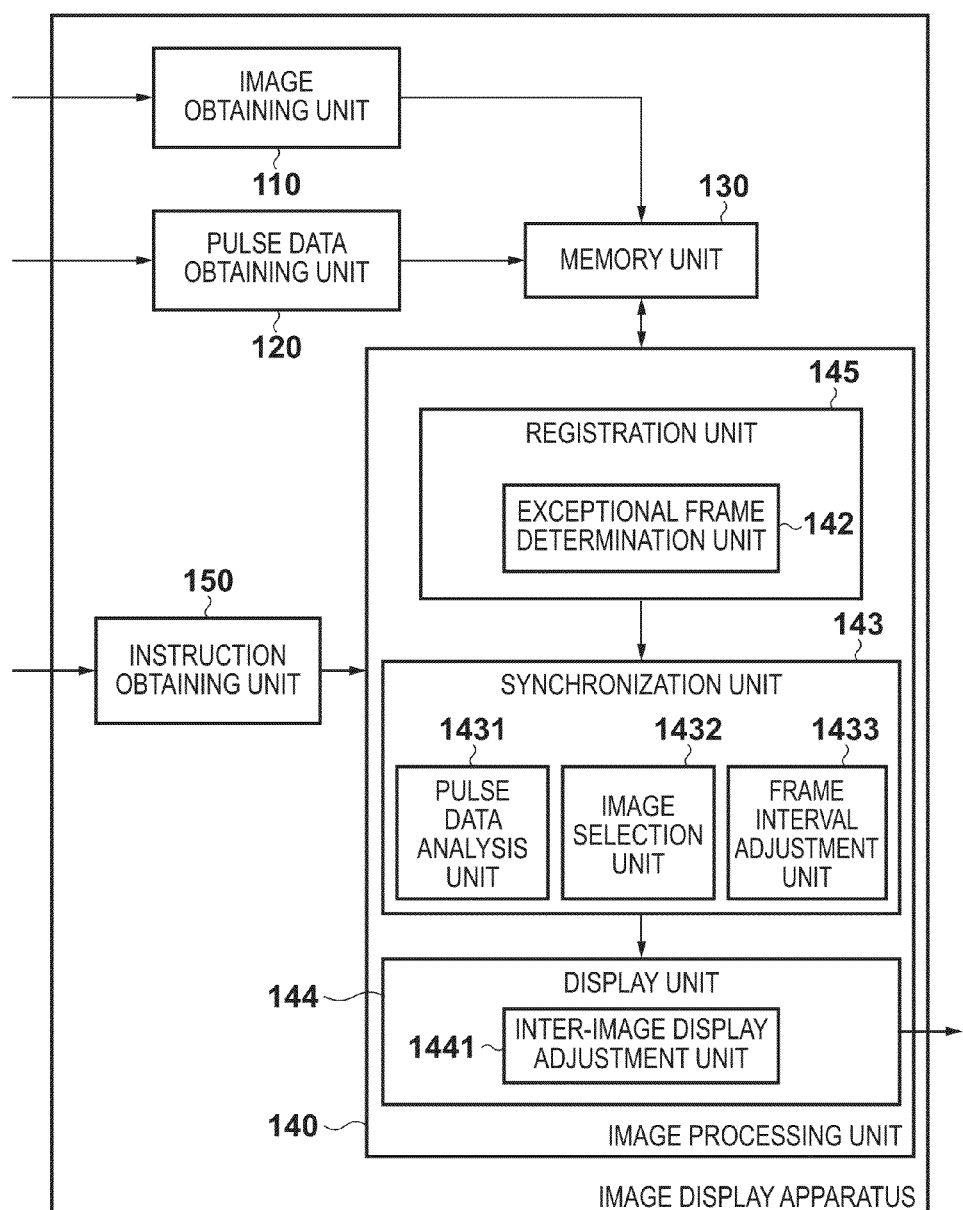
FIG. 11 is a block diagram showing an example of the functional arrangement of an image display apparatus 10 according to the third embodiment.
Figure 12:
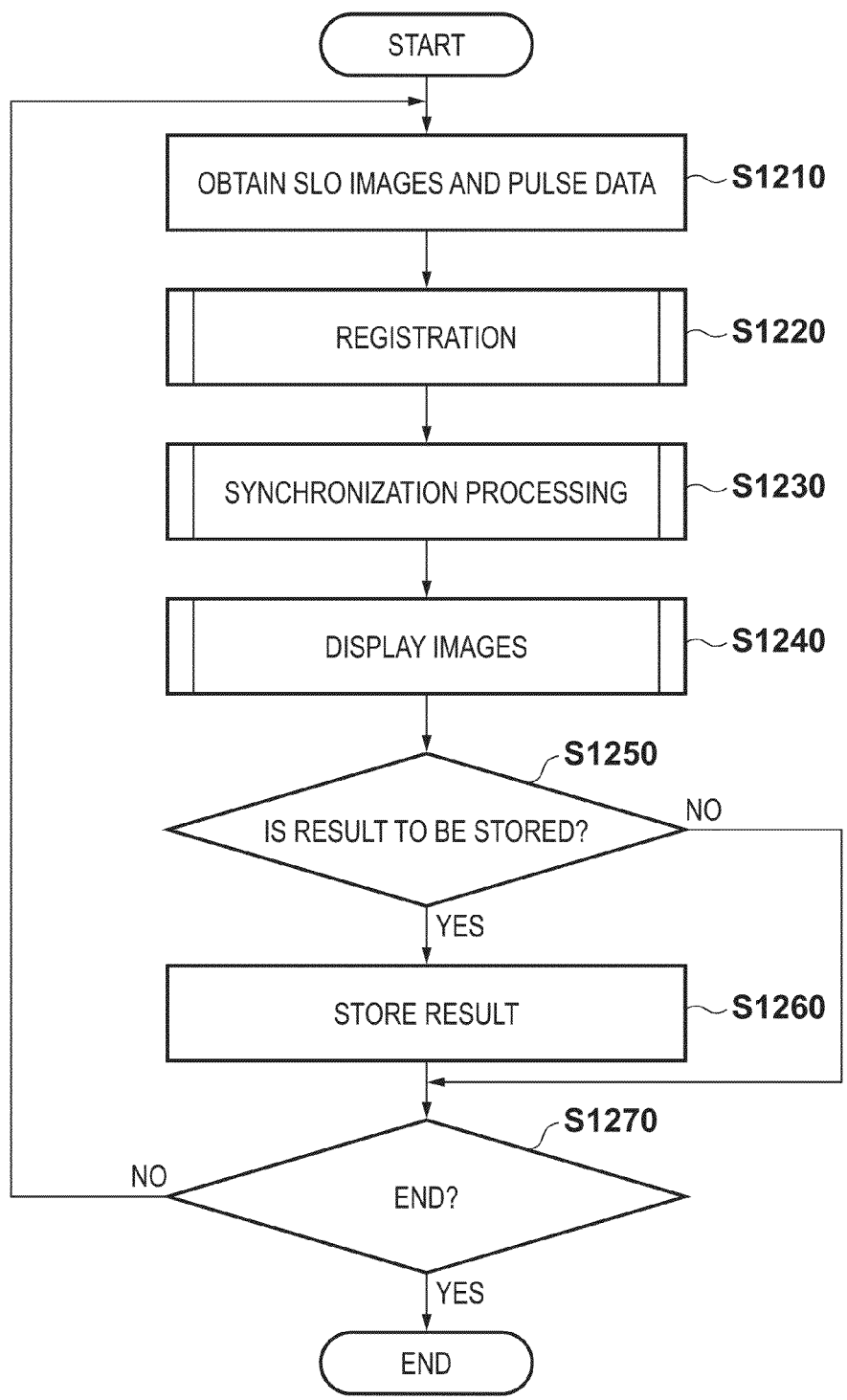
FIG. 12 is a flowchart illustrating processing executed by an image display apparatus 10 according to the third or fourth embodiment.

FIG. 11 is a functional block diagram showing an image display apparatus 10 according to the third embodiment. The third embodiment is different from the second embodiment (FIG. 8) in that the display unit 144 includes an inter-image display adjustment unit 1441. FIG. 12 is a flowchart illustrating image display processing according to the third embodiment. Steps except for step S1240 are the same as those in the second embodiment (steps S1210 to S1230 and S1250 to S1270 of FIG. 12 correspond to steps S910 to S930 and S950 to S970 of FIG. 9, respectively). Processing in step S1240 will be described below.

Figure 13:
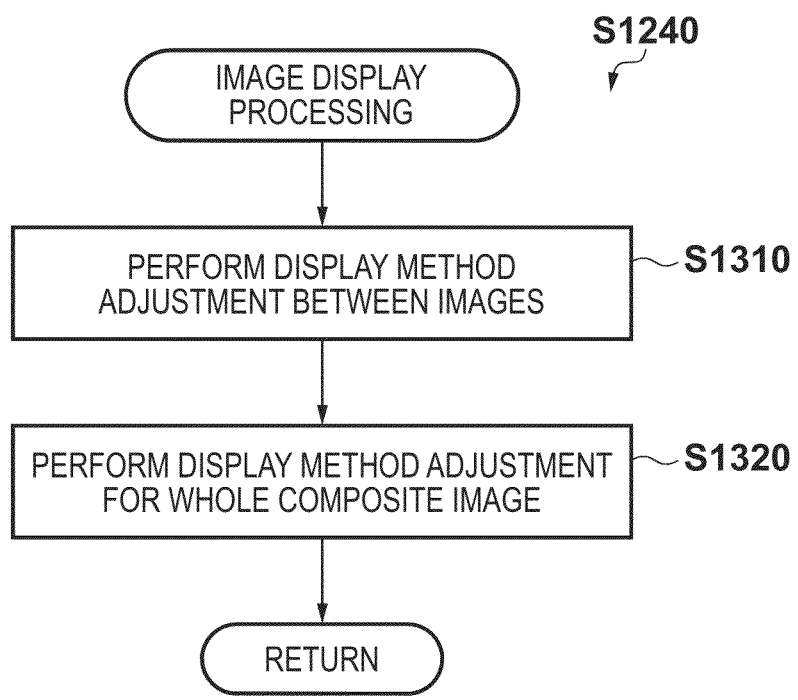
FIG. 13 is a flowchart illustrating processing executed in step S1240 according to the third embodiment.

<Step S1240> The inter-image display adjustment unit 1441 adjusts the luminance between the SLO moving images Di, and also adjusts the luminance between the wide field of view image W and each SLO moving image Di. Furthermore, in this embodiment, based on a user instruction obtained through an instruction obtaining unit 150, the display unit 144 interactively adjusts the display timing and magnification of the whole composite image of the wide field of view image W and the SLO moving images Di. The processing executed in step S1240 will be described in detail with reference to a flowchart shown in FIG. 13.

<Step S1310> The inter-image display adjustment unit 1441 adjusts the luminance between the SLO moving images Di, and also adjusts the luminance between the wide field of view image W and each SLO moving image Di. In this embodiment, the histogram of each SLO moving image Di is obtained, and the luminance values of the wide field of view image W and SLO moving images other than an SLO moving image Di with luminance characteristics which are closest to an ideal luminance average value Ga and luminance variance value Ja undergo linear transformation so that they coincide with a luminance average Gi and luminance variance Ji of the SLO moving image Di. The histogram may be calculated for an arbitrary frame, a plurality of arbitrary frames, or all the frames of the SLO moving image.

Note that the luminance adjustment method is not limited to this, and an arbitrary luminance adjustment method may be used. For example, the luminance values of the SLO moving image Di may be adjusted to coincide with the luminance statistics (luminance average and luminance variance) of the wide field of view image W or the SLO moving image Di obtained by capturing a schematic eye. Alternatively, a blood vessel area Vi is extracted from each SLO moving image Di using a known blood vessel extraction method. A histogram Kvi limited to the blood vessel area Vi is generated, and then the luminance values may be adjusted so that luminance statistics (average and variance) calculated based on the histogram Kvi coincide with specific values (Gv and Jv) which facilitate recognition of the blood vessel area Vi.

Alternatively, the moving images may be adjusted so that the luminance characteristics of the positions of objects (for example, a lesion of a blood vessel in an SLO moving image D1 and a normal blood vessel site in an SLO moving image D2) to be specifically compared and observed coincide with each other. In this case, for example, the following procedure is executed.

The user uses a pointing device (for example, clicks with a mouse) to designate the positions or ranges of the objects to be specifically compared and observed.

The inter-image display adjustment unit 1441 obtains the designated positions and ranges through the instruction obtaining unit 150, and adjusts the luminance values of the SLO moving images D1 and D2 so that the luminance characteristics (luminance averages and luminance variances) near the positions coincide with each other.

<Step S1320> The display unit 144 performs display method adjustment for the displayed composite image as a whole. In this embodiment, based on a user instruction obtained through the instruction obtaining unit 150, the display unit 144 interactively adjusts the magnification and playback speed of the whole composite image of the wide field of view image W and the SLO moving images Di.

Note that in this embodiment, display method adjustment between images and that for the whole composite image have been described. The function of the display unit 144, however, is not limited to them. For example, the instruction obtaining unit 150 may be able to adjust the luminance characteristic, magnification, and playback speed of each of the SLO moving images Di or the wide field of view image W alone. Alternatively, a display method may be adjusted for each frame or each region of interest (ROI).

As described above, the display unit 144 of the image display apparatus 10 according to the third embodiment performs luminance adjustment between the SLO moving images Di with different imaging positions, and that between the wide field of view image W and each SLO moving image Di. Since the images are displayed by adjusting not only the positional relationship and display timing but also the luminance between the SLO moving images Di with different imaging positions or between the wide field of view image W and each SLO moving image Di, it becomes possible to readily compare and observe blood cell kinetics and a change in blood vessel shape between the SLO moving images Di with different imaging positions.

[Fourth Embodiment]

In the fourth embodiment, a background image generation unit 1442 (FIG. 14) is added to the functional arrangement (FIG. 11) of the third embodiment. The background image generation unit 1442 is configured to generate a background image with high image quality by superimposing a wide field of view image W obtained as a moving image, and to select a representative frame from the wide field of view image W so as to match its position and luminance with those of the SLO moving images Di with different imaging positions. This enables to generate the wide field of view image W more suitable for the SLO moving images, thereby readily comparing and observing blood cell kinetics and a change in blood vessel shape between the SLO moving images Di with different imaging positions.

Figure 14:
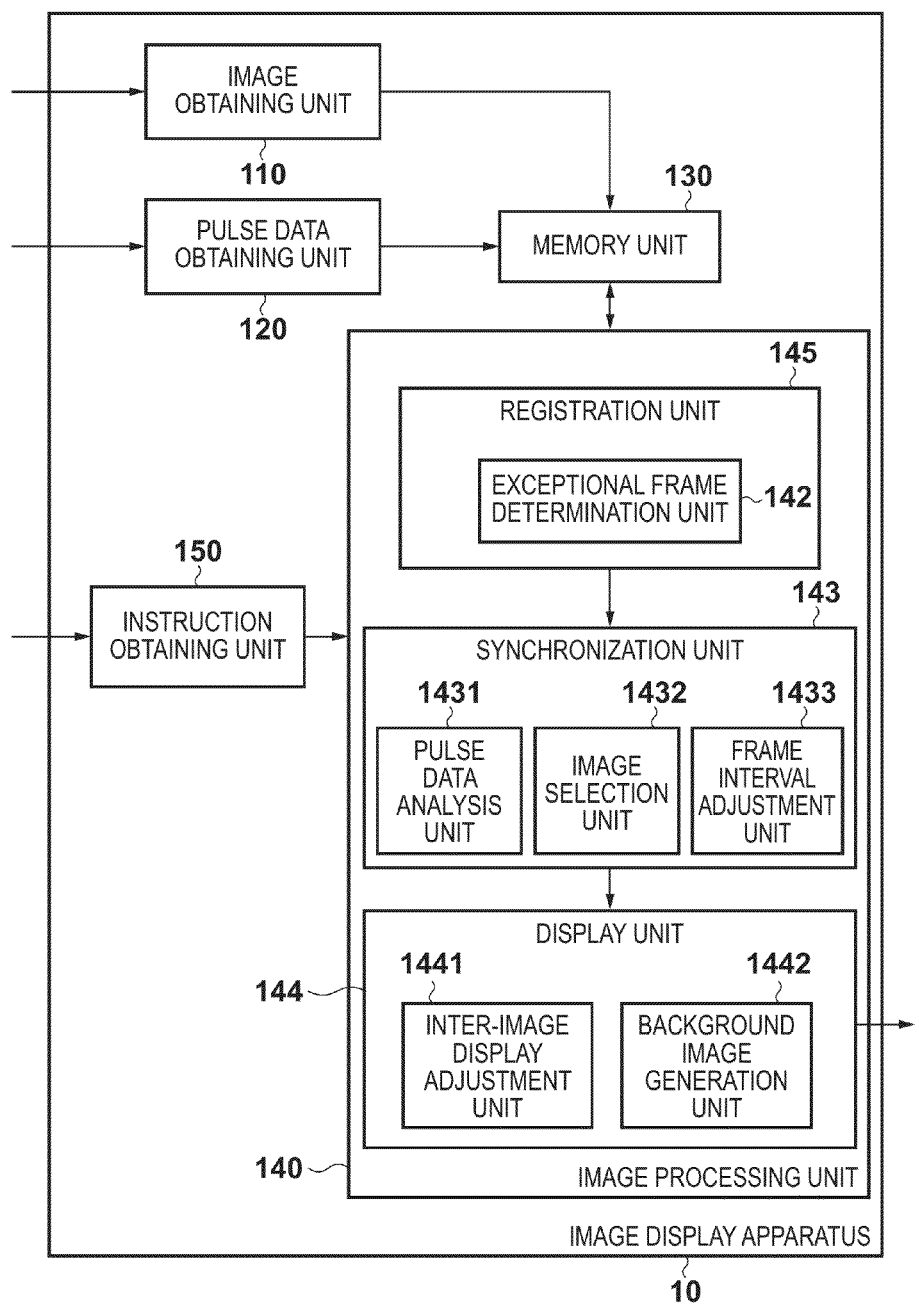
FIG. 14 is a block diagram showing an example of the functional arrangement of the image display apparatus 10 according to the fourth embodiment.

FIG. 14 is a functional block diagram showing an image display apparatus 10 according to the fourth embodiment. The fourth embodiment is different from the third embodiment in that a display unit 144 includes the background image generation unit 1442. An image display processing procedure according to the fourth embodiment is as shown in FIG. 12, and steps except for steps S1220, S1230, and S1240 are the same as those in the third embodiment. Processing in steps S1220, S1230, and S1240 according to the fourth embodiment will be described below.

<Step S1220> A registration unit 145 performs inter-frame registration for a moving image. In the fourth embodiment, the unit 145 performs exceptional frame determination and inter-frame registration for not only the SLO moving images Di but also the wide field of view image W according to the flowchart shown in FIG. 10B. The practical exceptional frame determination and inter-frame registration procedure is the same as that executed for the SLO moving images Di in the second embodiment.

<Step S1230> A synchronization unit 143 executes synchronization processing among all the moving images including the wide field of view image W (moving image) and the SLO moving images Di. The practical procedure of the synchronization processing between the wide field of view image W (moving image) and the SLO moving images Di is the same as that between the SLO moving images Di described in steps S610 to S650 of the first embodiment, in which a pulse section to be played back is extracted from each moving image.

<Step S1240> The background image generation unit 1442 generates a background image by superimposing a plurality of frames in the extracted pulse section of the wide field of view image W, or selecting a representative frame from the wide field of view image W among the plurality of frames of the extracted pulse section. The registration unit 145 performs registration between the SLO moving images Di and the background image generated by the background image generation unit 1442. Furthermore, an inter-image display adjustment unit 1441 adjusts the luminance values of the SLO moving images Di so as to match them with the luminance characteristics (luminance average and luminance variance) of the background image. Finally, based on an instruction obtained from the instruction obtaining unit 150, the display unit 144 performs display adjustment for the whole composite image of the wide field of view image W and the SLO moving images Di.

The processing executed in step S1240 will be described in detail with reference to a flowchart shown in FIG. 15. Processes in steps S1530 and S1540 of FIG. 15 are the same as those in steps S1310 and S1320 (FIG. 13) of the third embodiment, respectively.

<Step S1510> The background image generation unit 1442 generates a background image based on the wide field of view image W (moving image). As described above, in the fourth embodiment, exceptional frame determination and inter-frame registration processing has been executed for the wide field of view image W in step S1220, and frames of the wide field of view image have been selected not to include exceptional frames in step S1230. More specifically, a composite image is generated by averaging, in the frame direction, pixels of the wide field of view image having undergone inter-frame registration and synchronization processing.

Note that the background image generation method is not limited to this, and an arbitrary method may be used. If, for example, a representative frame is selected and used as a background image as described above, a total sum $\Sigma f$ of image similarities (for example, similarities of luminance characteristics) between each frame Wf of the wide field of view image W selected by the synchronization processing and all frames selected by the synchronization processing of each SLO moving image Di is obtained, and a wide field of view image frame Wf with a frame number for which the total sum $\Sigma f$ is largest is selected as a background image (representative frame).

<Step S1520> The registration unit 145 performs registration between the SLO moving images Di and the background image generated by the background image generation unit 1442. A practical registration method is the same as that described in steps S1021 and S1022 of the second embodiment.

As described above, in the fourth embodiment, the background image generation unit 1442 generates a background image with higher image quality by superimposing a plurality of frames of the wide field of view image W, and displays it as a wide field of view image, or selects, from the plurality of frames of the wide field of view image W, a representative frame so as to match its position and luminance with those of the SLO moving images Di with different imaging positions, and displays the selected frame as a wide field of view image. This enables to readily compare and observe blood cell kinetics and a change in blood vessel shape between the SLO moving images Di with different imaging positions.

As described above, according to the above-described embodiments, it is possible to display a plurality of moving images corresponding to a plurality of imaging positions (imaging areas) of a fundus under an almost equal influence of a difference in imaging conditions or the vital reaction of an object. The plurality of moving images are displayed at corresponding positions on the wide field of view image (a wide range image including the plurality of imaging areas) of the fundus. It is, therefore, possible to compare and observe kinetics and a shape change of tissue/cells in the plurality of moving images with different imaging areas while understanding the relationship with a normal site/anatomical site or a lesion outside the imaging areas of the moving images.

[Other Embodiments]

Although a plurality of moving images are synchronously displayed in the above-described embodiments, the present invention is not limited to this. A corresponding frame may be obtained from each moving image, and then displayed. If the image display apparatus 10 controls the display unit 144 to play back frame images frame by frame according to a user instruction, the user can readily compare frame images of the same pulse.

Although the embodiments have been described in detail, the present invention can adopt an embodiment in the form of, for example, a system, apparatus, method, program, or storage medium. More specifically, the present invention may be applied to a system constituted by a plurality of devices, or an apparatus comprising a single device.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-034536, filed Feb. 20, 2012, which is hereby incorporated by reference herein in its entirety.

The invention claimed is:

1. An image display apparatus comprising:
an obtaining unit that obtains a first moving image and a second moving image, first pulse data and second pulse data, and a wide field of view image, the first moving image and the second moving image being captured at different imaging positions of a fundus and being respectively associated with the first pulse data and the second pulse data based on a biomedical signal obtained in capturing the moving image, and the wide field of view image being obtained by capturing an area including the imaging positions of the first moving image and the second moving image;
a synchronous unit that executes processing for synchronizing display timing of the first moving image and the second moving image based on the first pulse data and the second pulse data; and
a display control unit that synchronously displays the first moving image and the second moving image on the wide field of view image on a display unit based on the display timing.

2. The apparatus according to claim 1, wherein the synchronous unit comprises a determination unit that determines an exceptional frame among a plurality of frames of each of the first moving image and the second moving image based on an image feature of each of the plurality of frames,
wherein the synchronous unit selects a section to be synchronously displayed from each of the first moving image and the second moving image so as to limit display of the exceptional frame.

3. The apparatus according to claim 2, wherein the synchronous unit selects the section to be synchronously displayed from sections in which phase of the pulse data is common to the first moving image and the second moving image and the number of exceptional frames is not larger than a predetermined number.

4. The apparatus according to claim 2, wherein the image feature is at least one of a luminance, an amount of image distortion, a signal to noise ratio, and an amount of movement between frames.

5. The apparatus according to claim 2, further comprising a registration unit that performs inter-frame registration using the image feature of each frame in each of first moving image and the second moving image,
wherein the determination unit determines the exceptional frame based on an image feature of a single frame before the registration, and determines the exceptional frame based on an image feature associated with a difference with respect to another frame after the registration.

6. The apparatus according to claim 5, wherein the determination unit determines the exceptional frame using the image feature used for the registration.

7. The apparatus according to claim 2, wherein the synchronous unit interpolates and adds or deletes a frame so that a difference in number of frames for one cycle of the pulse data in the section to be synchronously displayed between the first moving image and the second moving image falls within a predetermined range.

8. The apparatus according to claim 2, wherein the wide field of view image is a moving image, and
wherein the apparatus further comprises a generation unit that averages frames in the section to be displayed of the wide field of view image to generate a wide field of view image to be displayed on the display unit.

9. The apparatus according to claim 2, wherein the display control unit selects, among frames in the section to be displayed of the wide field of view image as a moving image, a frame having a highest image similarity with respect to the first moving image and the second moving image, and displays the selected frame as a wide field of view image on which the first moving image and the second moving image are superimposed.

10. The apparatus according to claim 1, further comprising an adjustment unit that performs adjustment so that the luminance characteristics of the first of moving image and the second moving image or those of the first moving image and the second moving image and the wide field of view image to be displayed by the display control unit coincide with each other.

11. The apparatus according to claim 10, wherein the adjustment unit performs adjustment so that the luminance characteristics of designated parts of the first moving image and the second moving image coincide with each other.

12. The apparatus according to claim 1, wherein the display control unit superimposes only a specific area extracted from the first moving image and the second moving image on the wide field of view image, and displays the obtained image.

13. The apparatus according to claim 1, wherein the first moving image, the second moving image, and the wide field of view image are images of a fundus obtained by a scanning laser ophthalmoscope including an aberration correction device, and
wherein the first moving image and the second moving image are images obtained by performing aberration correction by the aberration correction device, and the wide field of view image is an image obtained without undergoing aberration correction by the aberration correction device.

14. An imaging system comprising:
an image display apparatus comprising (a) an obtaining unit that obtains a first moving image and a second moving image, first pulse data and second pulse data, and a wide field of view image, the first moving image and the second moving image being captured at different imaging positions of a fundus and being respectively associated with the first pulse data and the second pulse data based on a biomedical signal obtained in capturing the moving image, and the wide field of view image being obtained by capturing an area including the imaging positions of the first moving image and the second moving image; (b) a synchronous unit that executes processing for synchronizing display timing of the first moving image and the second moving image based on the first pulse data and the second pulse data; and (c) a display control unit that synchronously displays the first moving image and the second moving image on the wide field of view image on a display unit based on the display timing; and
a scanning laser ophthalmoscope including an aberration correction device, which captures the first moving image, the second moving image, and the wide field of view image.

15. An image display method for an image display apparatus, the method comprising:
obtaining a first moving image and a second moving image, first pulse data and second pulse data, and a wide field of view image, the first moving image and the second moving image being captured at different imaging positions of a fundus and being respectively associated with the first pulse data and the second pulse data based on a biomedical signal obtained in capturing the moving image, and the wide field of view image being obtained by capturing an area including the imaging positions of the first moving image and the second moving image;

executing processing for synchronizing display timing of the first moving image and the second moving image based on the first pulse data and the second pulse data; and synchronously displaying the first moving image and the second moving image on the wide field of view image based on the display timing.

16. A non-transitory computer-readable storage medium storing a program for causing a computer to execute an image display method for an image display apparatus, the method comprising:

obtaining a first moving image and a second moving image, first pulse data and second pulse data, and a wide field of view image, the first moving image and the second moving image being captured at different imaging positions of a fundus and being respectively associated with the first pulse data and the second pulse data based on a biomedical signal obtained in capturing the moving image, and the wide field of view image being obtained by capturing an area including the imaging positions of the first moving image and the second moving image;

executing processing for synchronizing display timing of the first moving image and the second moving image based on the first pulse data and the second pulse data; and synchronously displaying the first moving image and the second moving image on the wide field of view image based on the display timing.

17. An image display apparatus comprising:

an obtaining unit configured to obtain a first moving image and a second moving image, and first pulse data and second pulse data, the first moving image and the second moving image being captured at different imaging positions of a fundus and being respectively associated with the first pulse data and the second pulse data based on a biomedical signal obtained in capturing the moving image;

a synchronous unit configured to execute processing for synchronizing display timing of the first moving image and the second moving image based on the first pulse data and the second pulse data; and a display control unit configured to synchronously display the first moving image and the second moving image on a display unit based on the display timing.

18. The apparatus according to claim 17, wherein the synchronous unit comprises a determination unit configured to determine an exceptional frame among a plurality of frames of each of the first moving image and the second moving image based on an image feature of each of the plurality of frames, wherein the synchronous unit selects a section to be synchronously displayed from each of the first moving image and the second moving image so as to limit display of the exceptional frame.

19. The apparatus according to claim 18, wherein the image feature is at least one of a luminance, an amount of image distortion, a signal to noise ratio, and an amount of movement between frames.

20. The apparatus according to claim 18, further comprising a registration unit configured to perform inter-frame registration using the image feature of each frame in each of the first moving image and the second moving image, wherein the determination unit determines the exceptional frame based on an image feature of a single frame before the registration, and determines the exceptional frame based on an image feature associated with a difference with respect to another frame after the registration.

* * * * *